US012269853B2

(12) United States Patent
Oggero-Eberhardt et al.

(10) Patent No.: US 12,269,853 B2
(45) Date of Patent: Apr. 8, 2025

(54) MODIFIED HUMAN ERYTHROPOIETIN

(71) Applicants: UNIVERSIDAD NACIONAL DEL LITORAL, Santa Fe-Pcia. de Santa Fe (AR); CONSEJO NACIONAL DE INVESTIGACIONES CIENTIFICAS Y TECNICAS (CONICET), Ciudad Autonoma de Buenos Aires (AR); UNIVERSDAD NACIONAL DE GENERAL SAN MARTIN, Billinghurst-Pcia. de Buenos Aires (AR)

(72) Inventors: Marcos Oggero-Eberhardt, Rafaela-Pcia. de Santa Fe (AR); Maria de los Milagros Burgi-Fissolo, Santa Fe-Pcia. de Santa Fe (AR); Aquiles Dorella, San Carlos de Bariloche-Pcia. de Rio N (AR); Gabriela I. Aparicio, Villa Bosch-Pcia. de Buenos Aire (AR); Marina Etcheverrigaray, Santa Fe-Pcia. de Santa Fe (AR); Camila Scorticati, Ciudad Autonoma de Buenos Aires (AR); Ricardo Kratje, Santa Fe-Pcia. de Santa Fe (AR)

(73) Assignees: UNIVERSIDAD NACIONAL DEL LITORAL, Santa Fe. de Santa Fe (AR); CONSEJO NACIONAL DE INVESTIGACIONES CIENTIFICAS Y TECNICAS (CONICET), Ciudad Autonoma de Buenos Aires (AR); UNIVERSDAD NACIONAL DE GENERAL SAN MARTIN

( * ) Notice: Subject to any disclaimer, the term of this patent is extended or adjusted under 35 U.S.C. 154(b) by 835 days.

(21) Appl. No.: 17/280,541

(22) PCT Filed: Sep. 26, 2019

(86) PCT No.: PCT/IB2019/058179
§ 371 (c)(1),
(2) Date: Mar. 26, 2021

(87) PCT Pub. No.: WO2020/065576
PCT Pub. Date: Apr. 2, 2020

(65) Prior Publication Data
US 2022/0220177 A1 Jul. 14, 2022

(30) Foreign Application Priority Data

Sep. 27, 2018 (AR) .............................. 20180102793

(51) Int. Cl.
C07K 14/505 (2006.01)
A61P 25/28 (2006.01)
C12N 15/85 (2006.01)

(52) U.S. Cl.
CPC ............ *C07K 14/505* (2013.01); *A61P 25/28* (2018.01); *C12N 15/85* (2013.01)

(58) Field of Classification Search
None
See application file for complete search history.

(56) References Cited

U.S. PATENT DOCUMENTS

2006/0035322 A1* 2/2006 Baker ........................ A61P 7/06
435/325
2007/0072795 A1 3/2007 Haselbeck et al.
2012/0094906 A1 4/2012 Guyon et al.

FOREIGN PATENT DOCUMENTS

WO 95/05465 A1 2/1995
WO 2004003176 A2 1/2004

OTHER PUBLICATIONS

S. Elliott, et al; Structural requirements for additional N-linked carbohydrate on recombinant human erythropoietin; Journal of Biological Chemistry; vol. 279; No. 16; Apr. 16, 2004; pp. 16854-16862; XP002657380.
International Search Report and Written Opinion for PCT/IB2019/058179 dated Dec. 13, 2019; 10 pages in English.

* cited by examiner

*Primary Examiner* — Julie Ha
*Assistant Examiner* — Tara L Martinez
(74) *Attorney, Agent, or Firm* — LUCAS & MERCANTI, LLP

(57) ABSTRACT

A modified human erythropoietin with an increased plasma half-life, with an erythropoietic activity of less than 0.5% in relation to a native erythropoietin, which maintains the neuroprotective and neuroplastic capacity, which comprises the mutation of at least one of the binding sites the homodimeric or heterodimeric receptor by incorporating consensus sites for N-glycosylation.

3 Claims, 19 Drawing Sheets
Specification includes a Sequence Listing.

Figure 5:
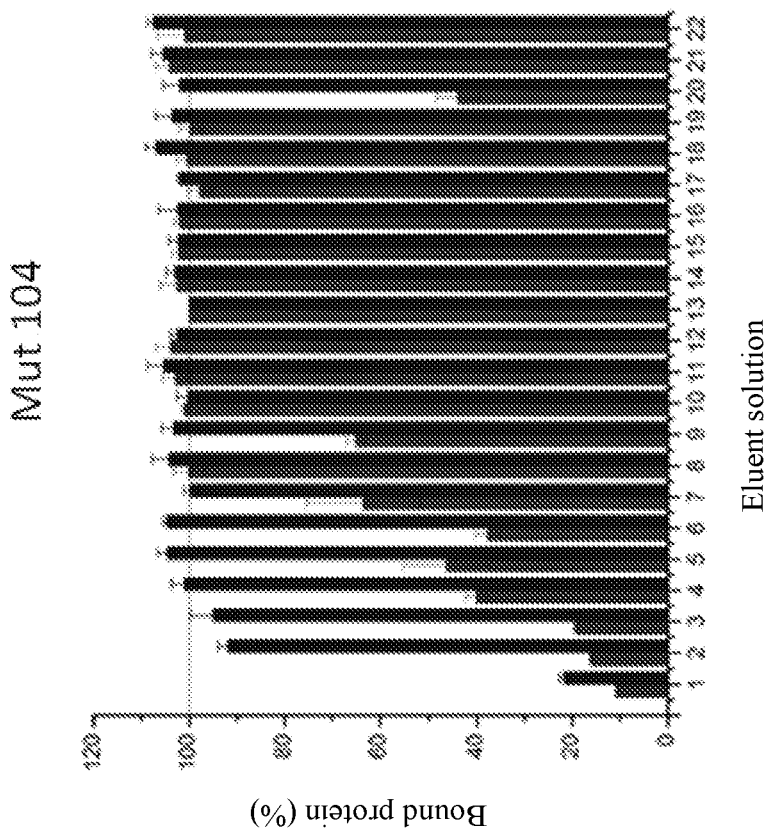
Figure 5:
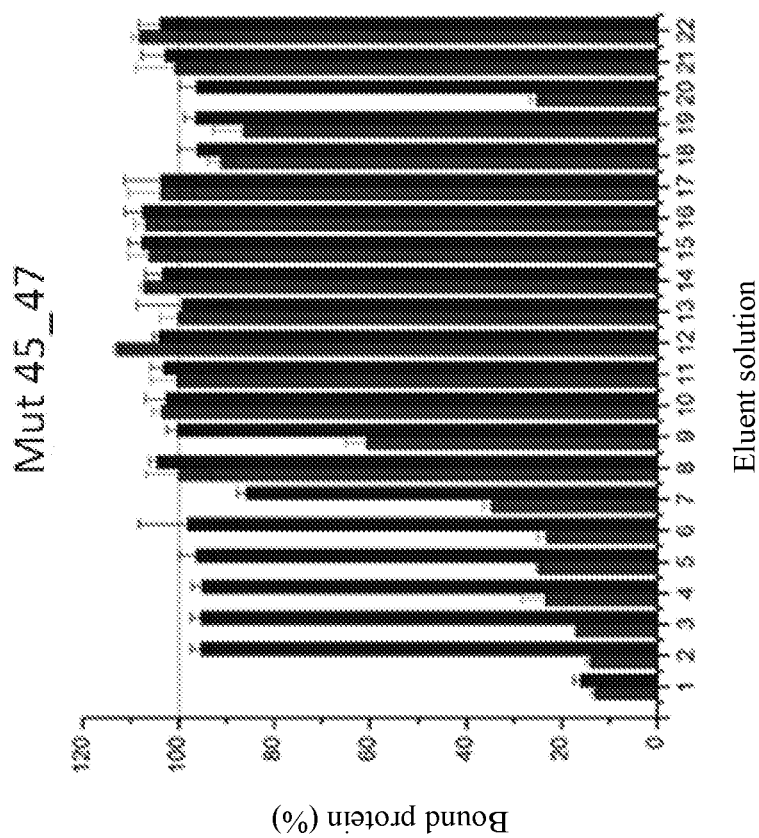

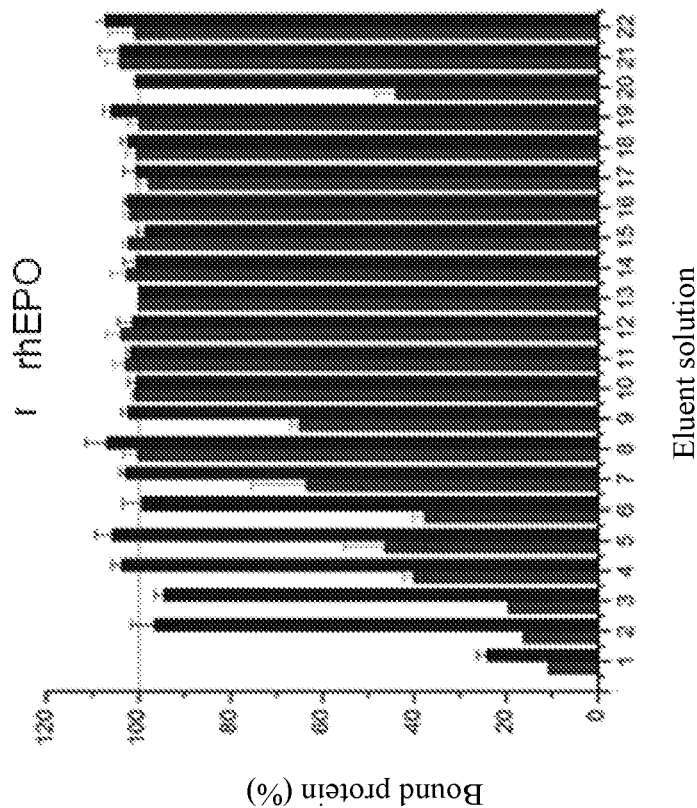
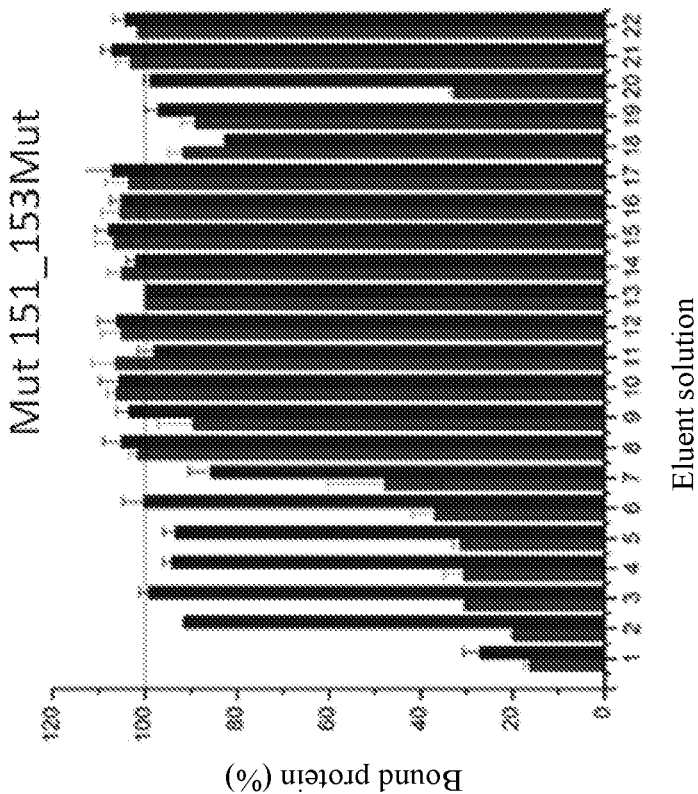
Figure 5 (continuation)

MODIFIED HUMAN ERYTHROPOIETIN

CROSS REFERENCE TO RELATED APPLICATION

This Application is a 371 of PCT/IB2019/058179 filed on Sep. 26, 2019, which claims priority of Argentinian Patent Application No. 20180102793 filed Sep. 27, 2018, both of which are incorporated herein by reference.

REFERENCE TO SEQUENCE LISTING SUBMITTED ELECTRONICALLY VIA EFS-WEB

The content of the electronically submitted sequence listing, file name: Second_Substitute_Sequence_Listing_06172024.txt; size: 30,718 bytes; and date of creation: Jun. 17, 2024, filed herewith, is incorporated herein by reference in its entirety.

TECHNOLOGY FIELD

This invention describes modified erythropoietin molecules with neuroplastic and neuroprotective capacity useful for the treatment of diseases of the central nervous system such as cerebrovascular accidents, neurotrauma, neuroinflammation and neurodegeneration.

STATE OF THE ART

Erythropoietin (EPO) is part of the type I cytokines superfamily that is characterized by its important pleiotropic activity [1]. This cytokine is one of the main regulators of erythropoiesis, acting synergistically with other molecules to promote the proliferation, differentiation and survival of erythroid lineage cell progenitors and maintain the mass of circulating erythrocytes [2].

Human EPO (hEPO) is a highly glycosylated protein, the molecular mass of which ranges from 30 to 39 kDa. It presents three consensus N-glycosylation sites and one O-glycosylation site [3] that can occur with a total degree of occupancy. The chains of sugars are composed of variable sequences of monosaccharides and a variable amount of sialic acid (SA) [4, 5]. The N-linked carbohydrates may contain two, three or four branches, each of which ends with a negatively charged SA molecule. For its part, the carbohydrate bound at the 0-glycosylation site can contain up to two SA molecules [6]. Glycosylation, especially the SA terminal of N-glycans, is fundamental for in vivo biological activity of EPO, but not for the in vitro receptor binding [7, 8]. That is why EPO molecules with lower glycosidic content have a high affinity for the EPO receptor (EPOR); however, their in vivo activity is diminished by an increase in their plasma clearance [8]. The degree of glycosylation of these cytokines affects their production efficiency, affinity for the receptor, plasma half-life, secretion and protein stability [5, 9].

Since the cloning of the hEPO gene in 1985, the knowledge on the cytokine biology has changed dramatically. One of the first advances was the discovery of a new biological action of the molecule, which extended its erythropoietic capacity and included several important physiological processes. Some of the most important ones are angiogenesis, vascular resistance regulation and—more importantly—cellular protection [10, 11]. Although the most important activity of erythropoietin is hematopoiesis, the presence of EPO and its receptor in various tissues and non-erythropoietic cells have confirmed the aforementioned hypothesis that EPO has multiple functions, and one of the most important ones is the cytoprotective function on cells of the central nervous system, heart, kidneys, gastrointestinal system, reproductive tract and endothelium [12], promoting cell proliferation, angiogenesis and inhibits cellular apoptosis [13]. These discoveries expanded the expectations of clinical use for the treatment of other pathologies such as heart attacks, cerebrovascular attacks and many others related to neuroprotection [14].

Neuroprotection can be defined as an approach to the maintenance and restoration of cellular interactions in the brain, resulting in maximum protection of neuronal functions [15]. The aim of neuroprotection is to prevent pathological neuronal loss in diseases of the central nervous system such as cerebrovascular accidents, neurotrauma, neuroinflammation and neurodegeneration.

Neurodegenerative diseases are a set of pathologies that affect the nervous system, and cause cognitive disorders, behavior disorders and changes in the body's regulation system. They are characterized by their chronicity and progressive evolution. These pathologies include diseases such as Parkinson's disease, different types of dementias, Alzheimer's disease, multiple sclerosis and Huntington's disease, among others, which constitute a problem from the medical, healthcare, social and economic point of view that all countries must face [16]. However, as the world's population ages, the impact of neurological disorders will be greater in both developed and developing countries. The burden of neurological disorders is reaching significant ratios in countries where the percentage of people over 65 years of age increases. Considering exclusively Alzheimer's disease, statistics indicate that approximately 44 million people live with dementia worldwide, a figure that is estimated to increase to 115 million in the year 2050. That is why this pathology is considered a global epidemic [17-19]. For this reason, numerous research groups around the world are engaged in the search for treatments that provide a cure to control this type of neurodegenerative pathologies.

The joint effort of numerous research groups has allowed research advances to deliver new and promising background on the origin of the problem and give hope to detect them in early stages, as well as to define more specific ways to attack them. However, even such efforts have not identified any biotherapeutic that can cure such pathologies. In this sense, the pharmaceutical market only offers medications indicated to delay the progress of these diseases once they have been detected but their benefits are often imperceptible, which is why it is necessary to develop new treatments. The success in coping with the health problem that neurodegenerative diseases represent today will depend, among other aspects, on the achievement of a therapy that generates benefits and lasting effects by favorably influencing the etiology or underlying pathogenesis, and preventing or delaying the onset of the disease or the gradual clinical deterioration in a safe, successful and effective manner. But in turn, it will be necessary to come up with an efficient technology accessible to large populations. The primary objective of the pharmaceutical industry in recent years has been to find compounds capable of attacking common key points in the development of many diseases of the central nervous system—such as apoptosis, oxidative stress, inflammation, metabolic dysfunction or compromised neuroplasticity.

In this research area, EPO plays a very important role due to its ability to develop a wide range of cellular responses in the brain, that are directly related to the protection and repair of cell damage [20]. EPO can induce neuroprotection through anti-inflammatory, antioxidant, anti-neurotoxic, angiogenic, neurotrophic, regenerative and antiapoptotic mechanisms.

In light of this, another extremely important advance in the study of EPO has been the identification of two different molecular sites associated with their erythropoietic and cytoprotective biological activities. These two activities are conferred through the binding of the cytokine to two different receptor systems; the homodimeric receptor (EPOR)2, responsible for the erythropoietic activity and the heterodimeric receptor EPOR-pCR, related to the cytoprotective activity [21]. These discoveries have been extremely important, as they have provided the necessary information to understand the pathways through which EPO develops its biological activities and, thus, allow the selective modulation of its erythropoietic or cytoprotective response, with the objective of avoiding or at least diminishing the side effects associated with the use of non-selective agents such as EPO or EPO analogues.

In this sense, although EPO is considered a safe and well tolerated drug in the treatment of anemia, when EPO is intended to be used as a cytoprotective agent in patients with cerebrovascular attacks or heart attacks, that is, as a neuroprotective agent in patients not suffering from anemia, its haematological effects should be considered as side effects, since it can cause polycythemia, hypertension and prothrombotic phenomena [22-25]. That is why the development of EPO analogues that selectively modulate their erythropoietic role and their cytoprotective role is highly relevant [14]. Following this purpose, various strategies have been designed to cancel the erythropoietic activity of the cytokine, maintaining its neuroprotective potential, through the application of chemical modifications on the molecule or the manipulation of the glycosidic content.

With respect to the strategies that employ chemical modifications on the EPO molecule, the carbamylation of seven lysine residues has been evaluated, that generates homocitrulline residues [26]. However, this methodology generates conformational changes in the protein that affect its function. Based on these results, different work groups have completely modified the recombinant hEPO (rhEPO) by carbamylation, obtaining a new molecule, called CEPO, which retains its cytoprotective activity, but lacks the erythropoietic activity [26-28]. However, high and numerous doses are required to obtain the desired objective and to maintain its therapeutic efficacy.

On the other hand, modifications have been made on rhEPO by manipulating its content of sialic acid (SA). In 2003, Erbayraktar et al [29] completely eliminated the residues of SA present in the ends of EPO glycosidic chains, thus generating the so-called Asialo EPO. This new EPO variant showed high in vitro activity. However, its in vivo neuroprotective activity was comparable to that obtained with rhEPO.

On the other hand, and with the aim of increasing the circulating half-life of the erythropoiesis-stimulating cytokine, Egrie and Brown [6] developed a protein that stimulates erythropoiesis: NESP, which is derived from hEPO and exhibits two additional N-glycosylation sites. This modification led to a three-fold increase in the half-life in plasma and its in vivo hematopoietic potency.

As regards the manipulation of the glucidic content, the inventors of the present application have obtained a rhEPO variant with similar characteristics to cerebral EPO (rh-NEPO), which is a combination of less acidic isoforms of rhEPO. This variant presented a neuroprotective activity equivalent to that of rhEPO and exhibited less than 4% hematopoietic activity [30]. However, rhNEPO's rapid plasma clearance is a disadvantage when proposing this molecule as a candidate for the treatment of chronic neurological diseases that require the plasma concentration to be sustained in time and to be adequate to exert its biological action. Moreover, given that the combination of glycoforms retains its in vitro erythropoietic activity, the administration of high and frequent doses to achieve the objective carries the risk of producing hematological effects, considered as adverse side effects.

Also, the state of the art shows many other efforts in obtaining molecules of erythropoietin or peptides derived from it that show neuroprotective activity and absence of erythropoietic activity. In this regard, patent US2015119325 describes an asialoerythropoietin (asialo-rhEPO) produced in plants. Patent applications US2009170759, US2003130197, MXPA02011727, and US2003130197 describe peptides that bind to the EPO receptor for the treatment of diseases that involve the central nervous system.

Document WO2004043382 describes a variant of the human erythropoietin polypeptide which contains an amino acid sequence having an amino acid difference in two or more different EPO modification regions and an enhanced erythropoietin activity. The invention aims at a human variant of the erythropoietin polypeptide which contains a human erythropoietin amino acid sequence having an amino acid difference in two or more different EPO modification regions and a moderate erythropoietin activity related to its cytoprotective capacity.

Patent US2011008363 describes different variants of EPO in which 1-10 amino acids have been deleted at the C-terminus of the protein. These are variants of lower molecular mass with reduced erythropoietic activity and preserved neuroprotective action.

Application US2007027068 describes glycopegylated EPO peptides. One of the mutated EPO peptides comprises the amino acid sequence (SEQ ID No.: 73) and has at least one mutation selected from the group consisting of Arg<139> to Ala <139>, Arg<143> to Ala <143> and Lys<154> to Ala <154>.

ES2457398 (T3) refers to a polynucleotide that encodes an EPO variant.

PCT WO2005025606 (A1) describes a modified EPO that incorporates oligosaccharides in order to increase erythropoietic activity and maintain its cytoprotective activity.

Likewise, WO2006127910 describes EPO with glycosylations to enhance the production of red blood cells. However, it is therein mentioned that it is also useful for treating neurodegenerative diseases since it exerts a cytoprotective function.

The application filed in Argentina (AR055654) describes a recombinant erythropoietin for the treatment of neurodegenerative disorders. The description details amino acids that could be modified to add glycosylation sites, and the modification of the following residues is emphasized: 87, 88, 90//30, 32, 87, 88, 90//24, 87, 88, 90//38, 87, 88, 90//83, 87, 88, 90. It aims at incorporating glycans in order to increase the circulating half-life to increase erythropoietic activity. The same aim is presented in the modifications introduced in patent WO9505465 which describes variants of erythropoietin that have additional glycosylation sites. Some of the sites mentioned in the patent are: 25, 30, 51, 57, 69, 88, 89, 136, 138.

In addition, the following substitutions are mentioned:
Asn<30>Thr<32> EPO;
Asn<51>Thr<53> EPO; Asn<57>Thr<59> EPO;

Asn<69> EPO;
Asn<69>Thr<71> EPO;
Ser<68>Asn<69>Thr<71> EPO;
Val<87>Asn<88>Thr<90> EPO;
Ser<87>Asn<88>Thr<90> EPO;
Ser<87>Asn<88>Gly<89>Thr<90> EPO;
Ser<87>Asn<88>Thr<90>Thr<92> EPO;
Ser<87>Asn<88>Thr<90>Ala<162> EPO;
Asn<69>Thr<72>Ser<87>Asn<88>Thr<90> EPO;
Asn<30>Thr<32>Val<87>Asn<88>Thr<90> EPO;
Asn<89>Ile<90>Thr<91> EPO;
Ser<87>Asn<89>Ile<90>Thr<91> EPO;
Asn<136>Thr<138> EPO;
Asn<138>Thr<140> EPO;
Thr<125> EPO; and
Pro<124>Thr<125> Epo.

Document WO2005103076 describes EPO variants having an even number of cysteine residues, preferably no more than four cysteine residues, or more preferably no more than two cysteine residues. Preferably, cysteine residues should be at positions 7, 29, 33, and 161, even more preferably at positions 7 and 161. The additional variants provided by this application include any mutation by addition at one or more of the following positions: 6, 29, 33, 45, 47, 48, 49, 61, 64, 74, 88, 92, 107, 109, 133, 135, 154, 157, and 158.

Application US2011003744 describes an erythropoietin formulation comprising this polyethylene glycol-conjugated protein or poly ethanolamine-conjugated protein through the enzymatically modified glycosidic residues in order to increase the hematopoietic properties.

Document MXPA05000063 describes a tissue-protective recombinant cytokine that lacks at least one of the effects of erythropoietin on the bone marrow; the tissue-protective recombinant cytokine would lack erythropoietic activity; more preferably the tissue-protective recombinant cytokine lacks all the effects of erythropoietin in the bone marrow. In the description it is mentioned that changes can be made in one or more amino acids, or deletions or additions to the EPO. In a preferred embodiment, the tissue-protective recombinant cytokine has one or more modifications in one or more of the following regions: VLQRY (amino acids 11-15 of native human erythropoietin, SEQ ID No.: 1) and/or TKVNFYAW (amino acids 44-51 of native human erythropoietin, SEQ ID No.: 2) and/or SGLRSLTTL (amino acids 100-108 of native human erythropoietin, SEQ ID No.: 3) and/or SNFLRG (amino acids 146-151 of native human erythropoietin, SEQ ID No.: 4). Other mutations can be provided in amino acids 7, 20, 21, 29, 33, 38, 42, 59, 63, 67, 70, 83, 96, 126, 142, 143, 152, 153, 155, 156, and 161 of SEQ ID No.: 10. These other mutations may be unique or additional to at least one mutation in at least one of the previously mentioned regions. In certain embodiments, the changes in one or more amino acids of TKVNFYAW (amino acids 44-51 of native human erythropoietin, SEQ ID No.: 2) result in a modified erythropoietin molecule with partial function, i.e., with less erythropoietic activity than rhEPO. In other embodiments, the changes in one or more amino acids of SGLRSLTTL (amino acids 100-108 of native human erythropoietin, SEQ ID No.: 3), there are even modifications in the content of sialic acid or molecules lacking glycans or modifications in carbohydrates such as oxidation, reduction or variants with chemical modifications such as nitration, acylation, succinylation, biotinylation, iodination and carbamylation. There is no reference to the addition of new glycans in the sites responsible for the erythropoietic activity aiming at reducing or blocking it.

It is possible to appreciate that the efforts described in the state of the art developed up to now have not yielded successful results in obtaining an erythropoietin that shows neuroprotective activity and absence of erythropoietic activity. This invention presents new hEPO muteins that have demonstrated neuroprotective and neurotrophic effects. These muteins were obtained by an original process that modifies the hEPO molecule through the generation of new consensus sites for N-glycosylation on the hEPO molecular region responsible for its binding to homo- and heterodimeric receptors. Unexpectedly, the new hEPO muteins lack erythropoietic activity but their neuroprotective/neuroplastic activity is unaltered, or even improved and, in turn, they present improvements in their pharmacokinetic properties. The modifications of the original EPO are minimal, which allows keeping a great resemblance with the structure of the natural protein.

Brief Outline of the Invention

This invention describes a modified human erythropoietin with absence or reduction of its erythropoietic activity, preferably with up to 0.5% of erythropoietic activity with regard to human erythropoietin, longer half-life in plasma, which maintains its neuroprotective and neuroplastic capacity. The binding to at least one of the homo- or heterodimeric receptors of this modified human erythropoietin is partially or completely cancelled. This invalidation comprises the mutation of one of the binding sites to homo- or heterodimeric receptors by the incorporation of consensus sites for N-glycosylation.

In a preferred embodiment of this invention, the modified human erythropoietin has the following mutations: Tyr15Asn and Leu17Thr, and comprises SEQ ID No. 2.

In a preferred embodiment of this invention, the modified human erythropoietin has the following mutations: Lys45Asn and Asn47Thr, and comprises SEQ ID No. 4.

In a preferred embodiment of this invention, the modified human erythropoietin has the following mutations: Glu62Asn and Trp64Thr, and comprises SEQ ID No. 8.

In a preferred embodiment of this invention, the modified human erythropoietin has the following mutations: Gln65Asn and Leu67Thr, and comprises SEQ ID No. 10.

In a preferred embodiment of this invention, the modified human erythropoietin has the following mutations: Glu72Asn and Val74Thr, and comprises SEQ ID No. 12.

In a preferred embodiment of this invention, the modified human erythropoietin has the following mutations: Arg76Asn and Gln78Thr, and comprises SEQ ID No. 14.

In a preferred embodiment of this invention, the modified human erythropoietin has the following mutations: Ala98Asn and Ser100Thr, and comprises SEQ ID No. 16.

In a preferred embodiment of this invention, the modified human erythropoietin has the following mutation: Ser104Asn, and comprises SEQ ID No. 18.

In a preferred embodiment of this invention, the modified human erythropoietin has the following mutations: Thr106Asn and Leu108Thr, and comprises SEQ ID No. 20.

In a preferred embodiment of this invention, the modified human erythropoietin has the following mutation: Leu149Thr, and comprises SEQ ID No. 22.

In a preferred embodiment of this invention, the modified human erythropoietin has the following mutations: Gly151Asn and Leu153Thr, and comprises SEQ ID No. 24.

The modified human erythropoietin of this invention has an erythropoietic activity of up to 1% with regard to human erythropoietin. Preferably, it has up to 0.5% erythropoietic activity with regard to human erythropoietin. More preferably, it has up to 0.2% erythropoietic activity with regard to human erythropoietin.

On the other hand, this invention describes nucleic acids comprising the nucleotide sequences of the erythropoietin of this invention. Also, the DNA sequences encoding each of the described and generated muteins are outlined. These DNA sequences are SEQ ID No. 1, SEQ ID No. 3, SEQ ID No. 7, SEQ ID No. 9, SEQ ID No. 11, SEQ ID No. 13, SEQ ID No. 15, SEQ ID No. 17, SEQ ID No. 19, SEQ ID No. 21, and SEQ ID No. 23. In an alternative embodiment of this invention, these nucleic acids are vectors for transforming cells, or are expression vectors or lentiviral vectors.

In a preferred embodiment of this invention, the nucleic acid sequence encoding the modified human erythropoietin of this invention is SEQ ID No. 1.

In a preferred embodiment of this invention, the nucleic acid sequence encoding the modified human erythropoietin of this invention is SEQ ID No. 3.

In a preferred embodiment of this invention, the nucleic acid sequence encoding the modified human erythropoietin of this invention is SEQ ID No.7.

In a preferred embodiment of this invention, the nucleic acid sequence encoding the modified human erythropoietin of this invention is SEQ ID No. 9.

In a preferred embodiment of this invention, the nucleic acid sequence encoding the modified human erythropoietin of this invention is SEQ ID No. 11.

In a preferred embodiment of this invention, the nucleic acid sequence encoding the modified human erythropoietin of this invention is SEQ ID No. 13.

In a preferred embodiment of this invention, the nucleic acid sequence encoding the modified human erythropoietin of this invention is SEQ ID No. 15.

In a preferred embodiment of this invention, the nucleic acid sequence encoding the modified human erythropoietin of this invention is SEQ ID No. 17.

In a preferred embodiment of this invention, the nucleic acid sequence encoding the modified human erythropoietin of this invention is SEQ ID No. 19.

In a preferred embodiment of this invention, the nucleic acid sequence encoding the modified human erythropoietin of this invention is SEQ ID No. 21.

In a preferred embodiment of this invention, the nucleic acid sequence encoding the modified human erythropoietin of this invention is SEQ ID No. 23.

Also, this invention describes genetically modified cells with any of the DNA sequences selected from the set comprised by SEQ ID No. 1, SEQ ID No. 3, SEQ ID No. 7, SEQ ID No. 9, SEQ ID No. 11, SEQ ID No. 13, SEQ ID No. 15, SEQ ID No. 17, SEQ ID No. 19, SEQ ID No. 21, and SEQ ID No. 23; wherein this genetically modified cell is capable of expressing the modified erythropoietin of this invention. In a preferred embodiment, this genetically modified cell is a plant cell, or an animal cell or any cellular host that allows the addition of N-glycans. Preferably, this cell is derived from an animal cell line. Preferably, this cell line is selected from the set comprised by CHO.K1, HEK293, NS0, BHK-21, and HeLa.

On the other hand, this invention describes a process to obtain modified human erythropoietin comprising the following steps:
 a. Provide the nucleic acid sequences that encode said modified human erythropoietin;
 b. Build at least one co-transfection vector of packaging cells;
 c. Co-transfect packaging cells that produce lentiviral particles containing this nucleic acid sequence that encodes said modified human erythropoietin;
 d. Harvest these lentiviral particles produced by the packaging cells of step c-;
 e. Transduce cells capable of expressing modified human erythropoietin with said lentiviral particles of step d-;
 f. Select the cells in step e- that include the nucleic acid sequence encoding the modified human erythropoietin;
 g. Culture the cells from step f- so that they express said modified human erythropoietin; and
 h. Isolate and purify said modified human erythropoietin.

Wherein in said step a, the nucleic acid sequences are selected from the set comprised by SEQ ID No. 1, SEQ ID No. 3, SEQ ID No. 7, SEQ ID No. 9, SEQ ID No. 11, SEQ ID No. 13, SEQ ID No. 15, SEQ ID No. 17, SEQ ID No. 19, SEQ ID No. 21, and SEQ ID No. 23.

Wherein step b includes a vector that allows the entry of the lentiviral particle into the cell, a vector encoding a matrix protein, capsid, lentiviral protease, reverse transcriptase and integrase, a transfer vector comprising the modified human erythropoietin sequence, and a vector that induces the nuclear export of the transfer vector.

Wherein in said Step e- said cells are selected from the set comprising CHO.K1, HEK293, NS0, BHK-21, and HeLa.

Wherein said Step h- is a purification by immunoaffinity that includes an anti-rhEPO antibody, and an eluent.

Wherein said eluent is selected from the group comprising glycine, acetic acid—NaCl, acetate salts, citric acid, phosphate salts, ethanol, isopropyl alcohol, dioxane, ethylene glycol, Tris-HCl, and their mixtures. Preferably, this eluent is selected from the group comprising glycine, acetic acid-NaCl. More preferably, the eluent is selected from the group comprising 0.1 M glycine (pH=2); 0.15 M glycine (pH=2.5), and 0.2 M acetic acid, 0.15 M NaCl (pH=3).

BRIEF OUTLINE OF THE FIGURES

Figure 1:
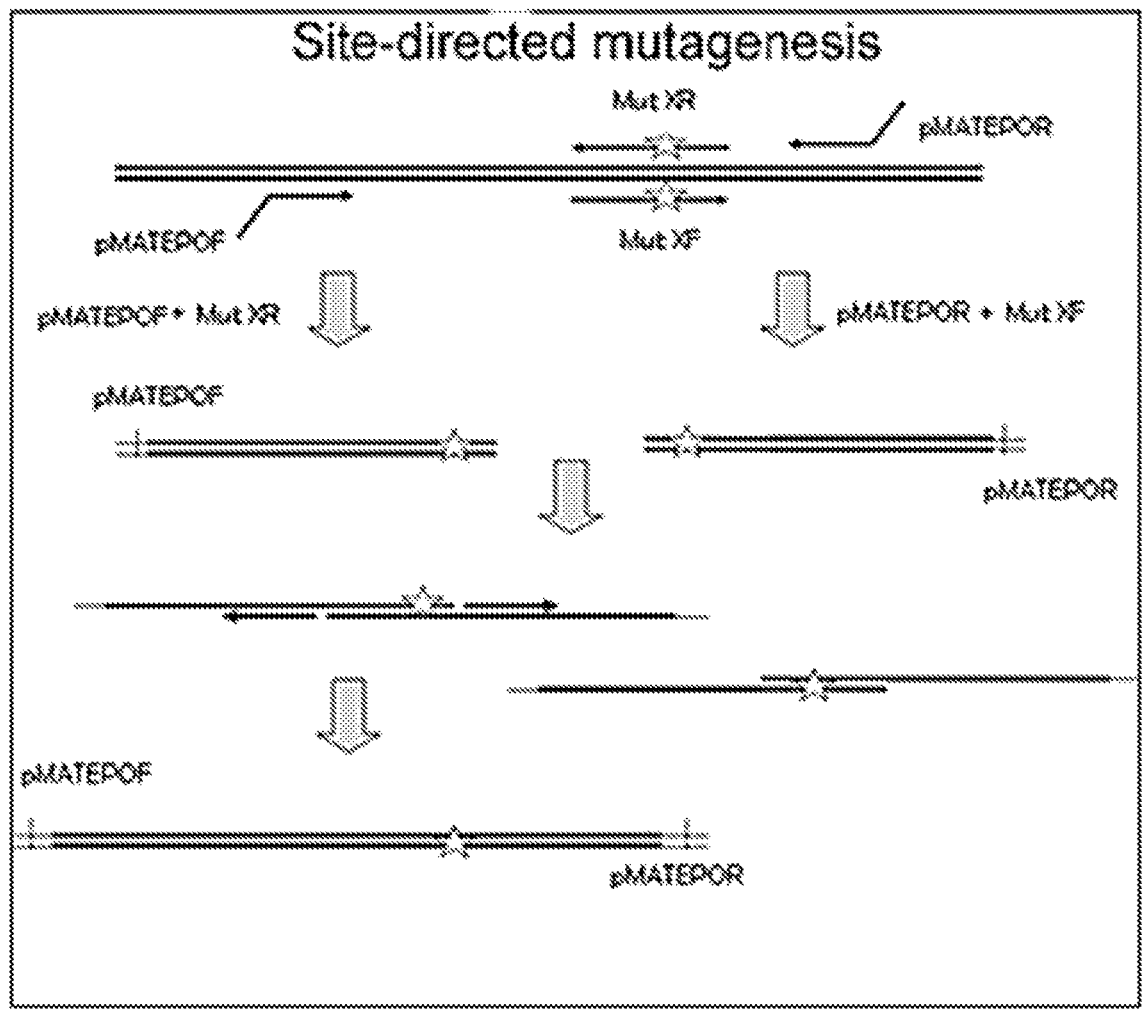

FIG. 1. Scheme of the sequence of steps to obtain the 12 hEPO muteins through site-directed mutagenesis.

Figure 2:
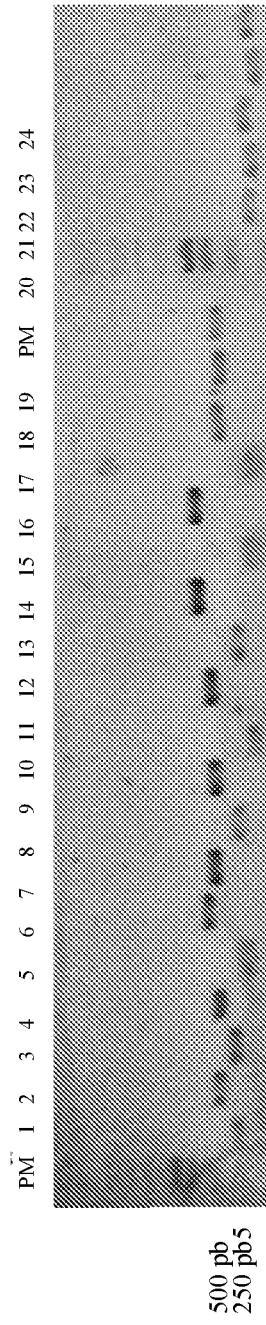

FIG. 2. Analysis of the fragments obtained in each of the PCR reactions using agarose gels. a—Fragments obtained from PCR1. b—Fragments obtained from PCR2.

Figure 3:
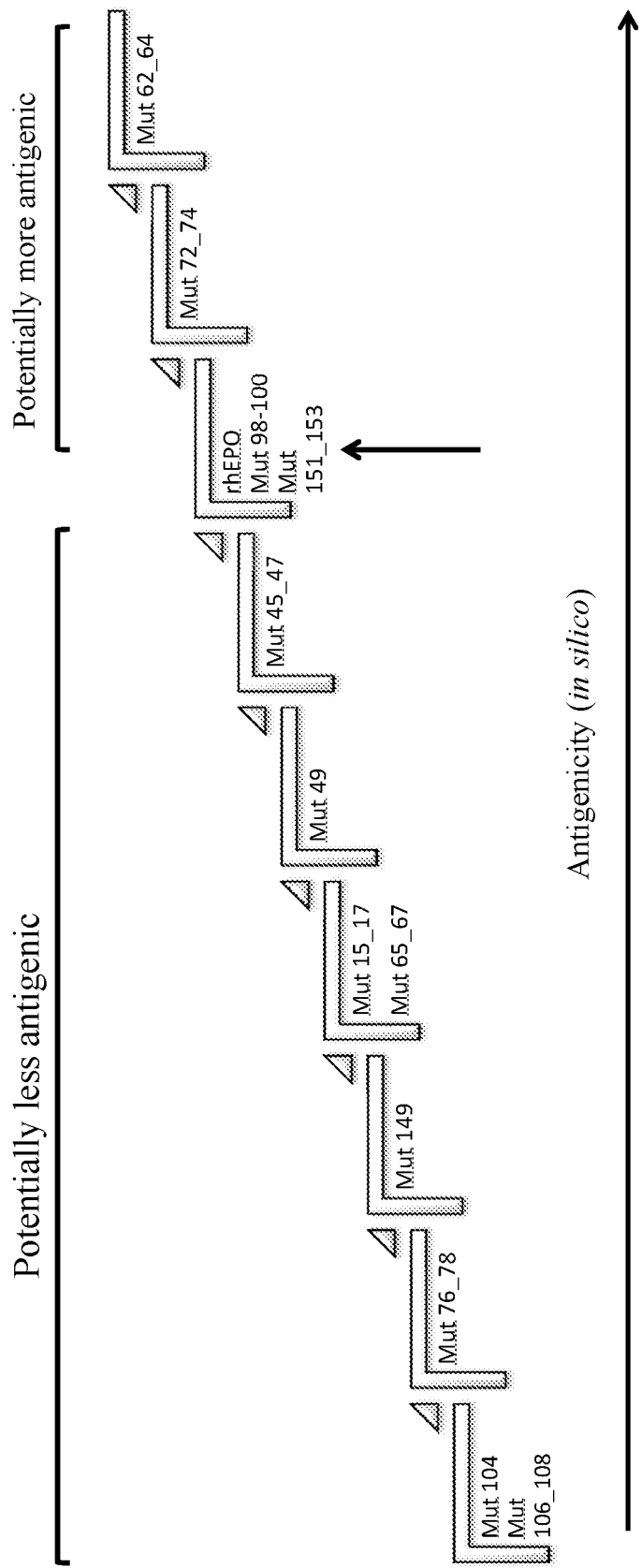

FIG. 3. In silico analysis of the potential antigenicity of hEPO muteins and the unmodified molecule using IEDB database.

Figure 4:
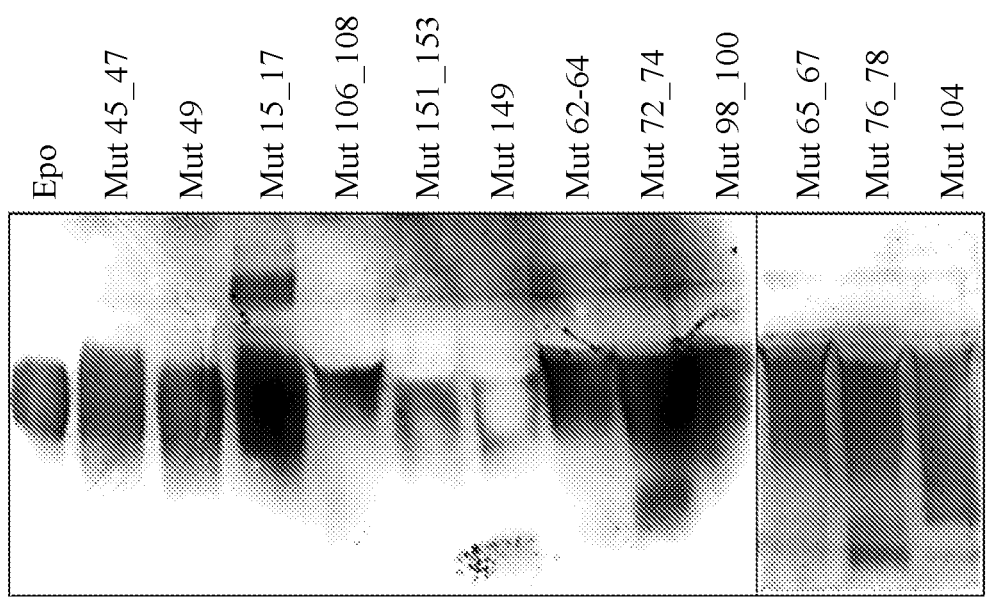

FIG. 4. Western Blot confirming the insertion of the new N-glycosylation sites.

FIG. 5. Elution capacity of rhEPO molecule or its muteins evaluated by ELISA sandwich technique.
 Protocol A (elution capacity after complex Ag—Ac is formed).
 Protocol B (preservation degree of the binding capacity to the molecules of interest after treating mAb with different eluents).

Figure 6:
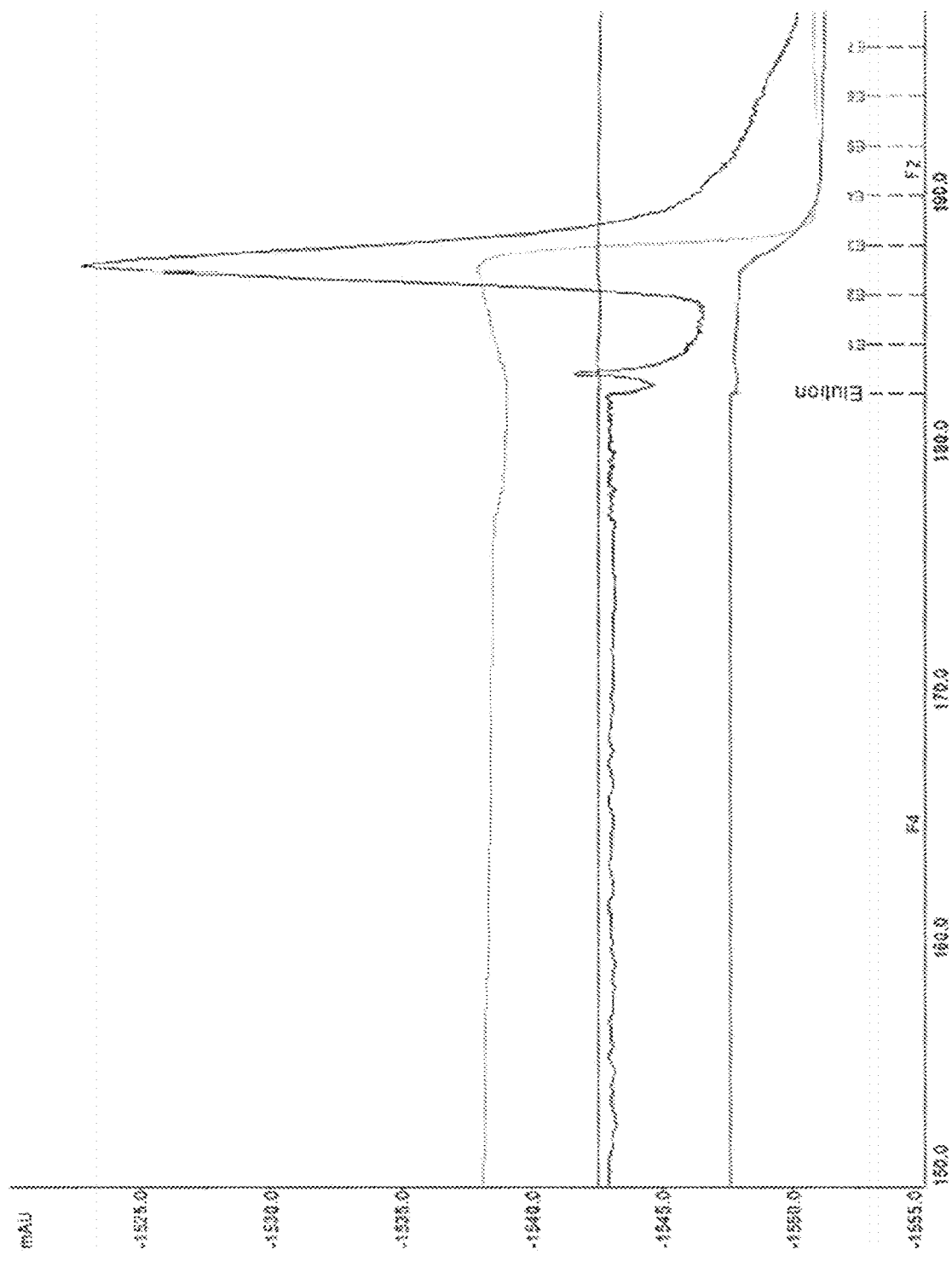

FIG. 6. Purification of hEPO mutein Mut 104 through immunoaffinity chromatography (IAC) using mAb 2B2.
 A—Complete chromatogram obtained during purification of hEPO mutein Mut 104.
 B—Scaling-up of chromatogram A elution zone.

Figure 7:

FIG. 7. Evaluation of mutein Mut 104 purification through immunoaffinity chromatography (IAC) using 0.15 M glycine (pH 2.5) as eluent solution. Samples: 1—Seeding, 2—Flowthrough, 3—Washing 1, 4—Washing 2, 5—Washing 3, 6—Mixture of elution fractions, 7—rhEPO standard (Zelltek S. A.).

Figure 8:
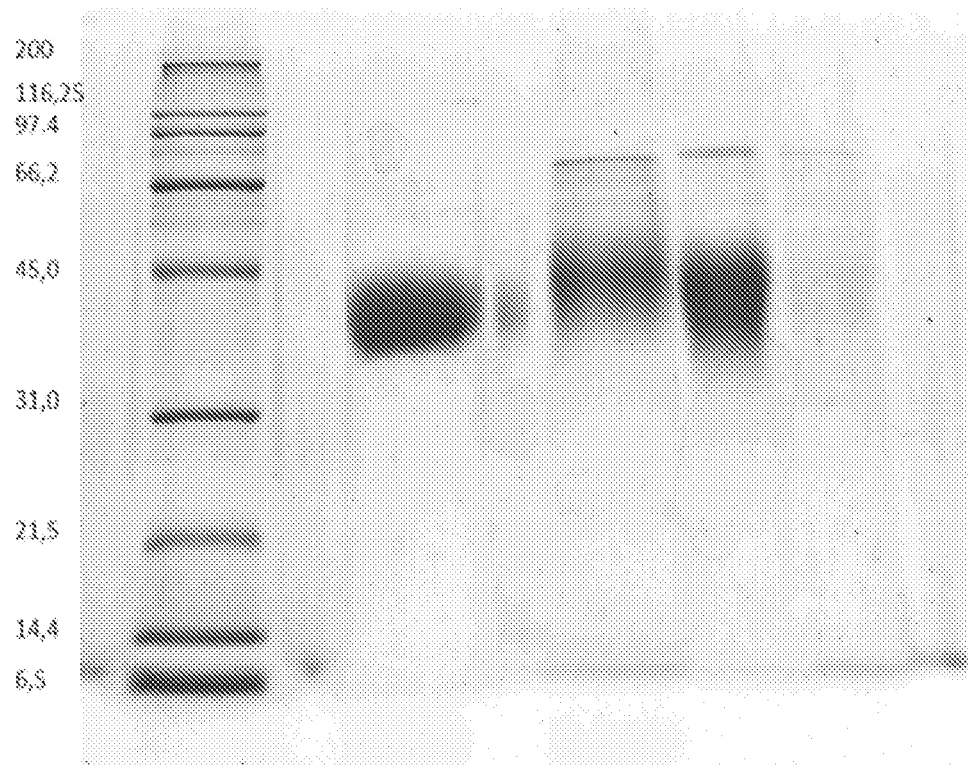

FIG. 8. Purity analysis in eluates obtained after immunoaffinity chromatography (IAC) of hEPO muteins. Samples: 1—Molecular mass marker, 2—rhEPO standard (Zelltek S. A.), 3—Eluate Mut 45_47, 4—Eluate Mut 104, 5—Eluate Mut 151_153.

Figure 9:
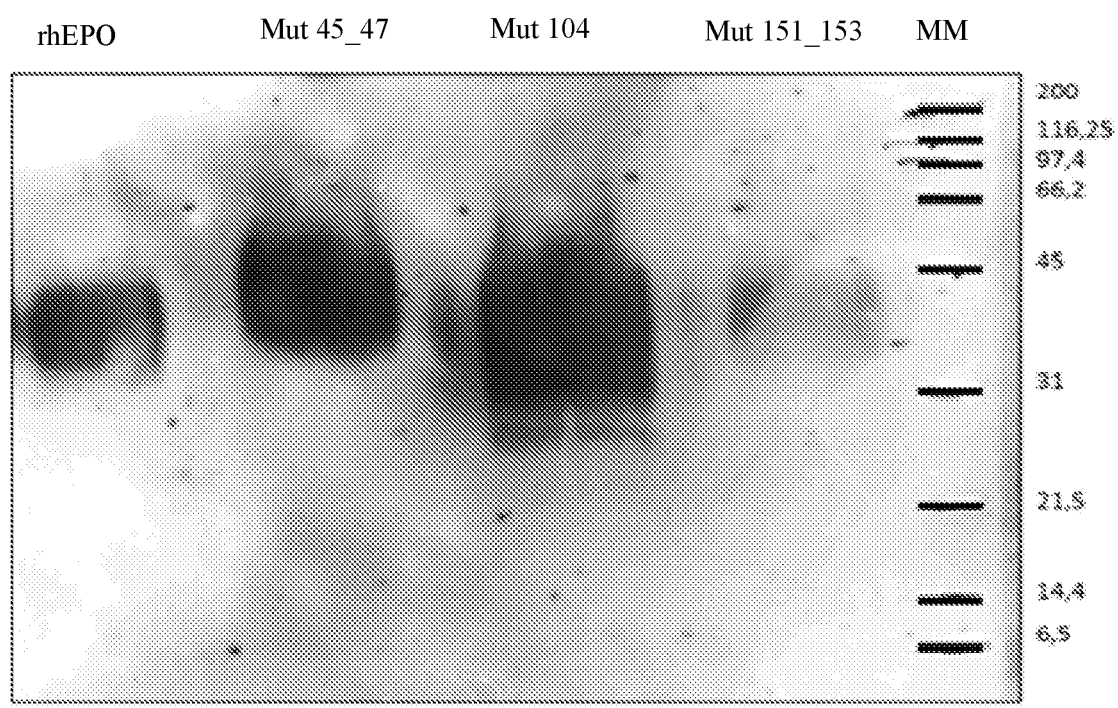

FIG. 9. Determination of apparent molecular masses of hEPO muteins. MM: Molecular mass marker.

Figure 10:
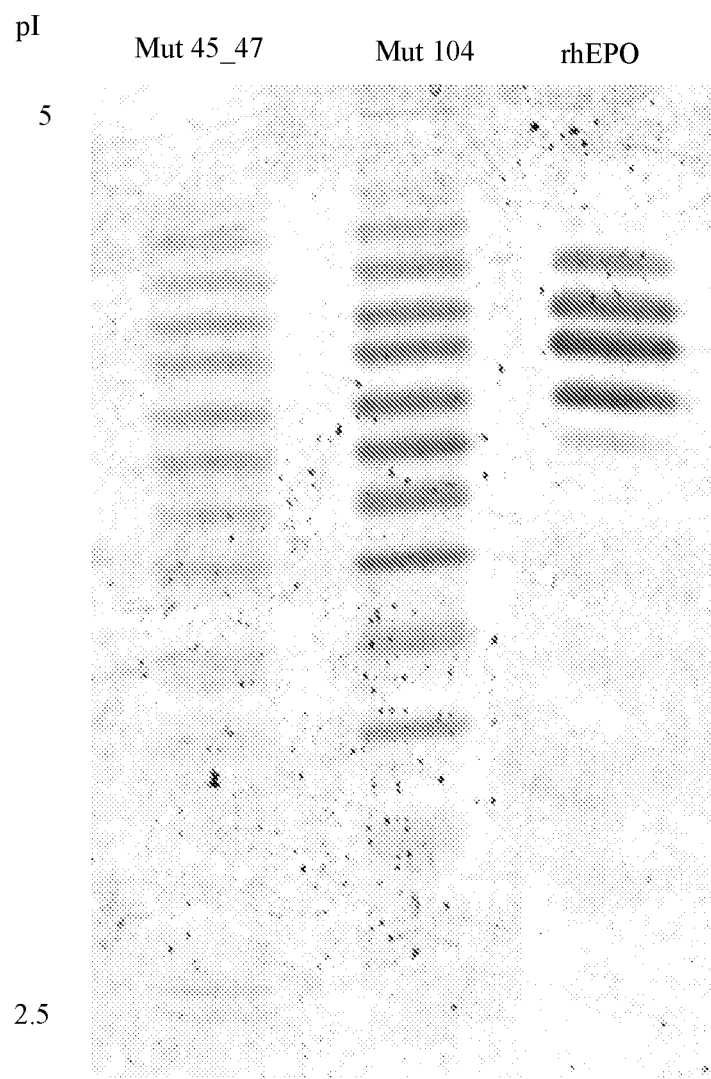

FIG. 10. IEF of hEPO muteins purified by immunoaffinity chromatography (IAC). Samples: 1—Mut 45_47, 2—Mut 104, 3-rhEPO standard (Zelltek S. A).

Figure 11:
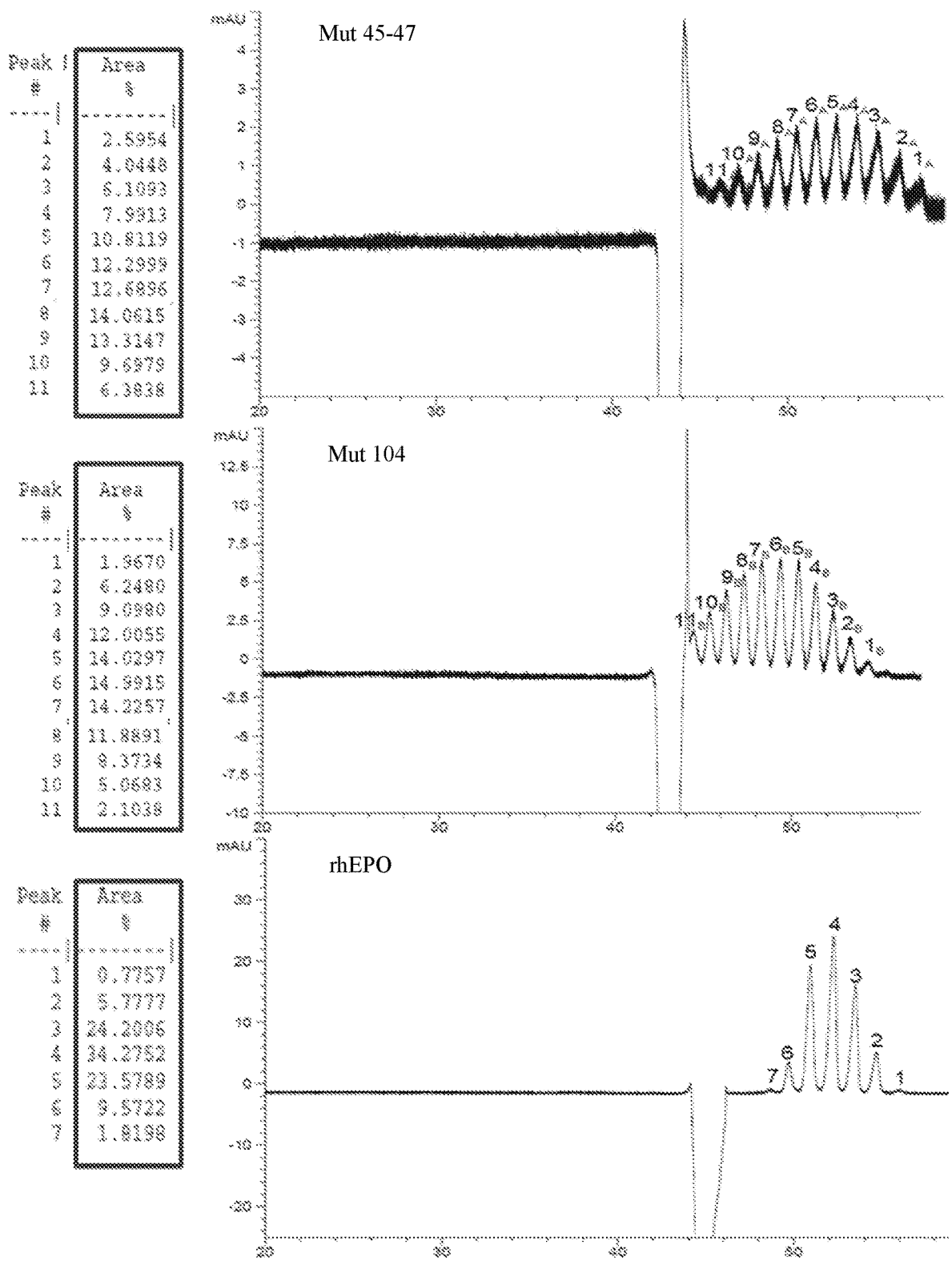

FIG. 11. ECZ electropherograms obtained for rhEPO and its muteins. A: Mut 45_47; B: Mut 104; C: rhEPO. The term "Peak" corresponds to each peak assigned in the ECZ electropherogram, and "Area" (%) represents the percentage of each isoform, calculated by integrating the area under the curve of each peak.

Figure 12A:
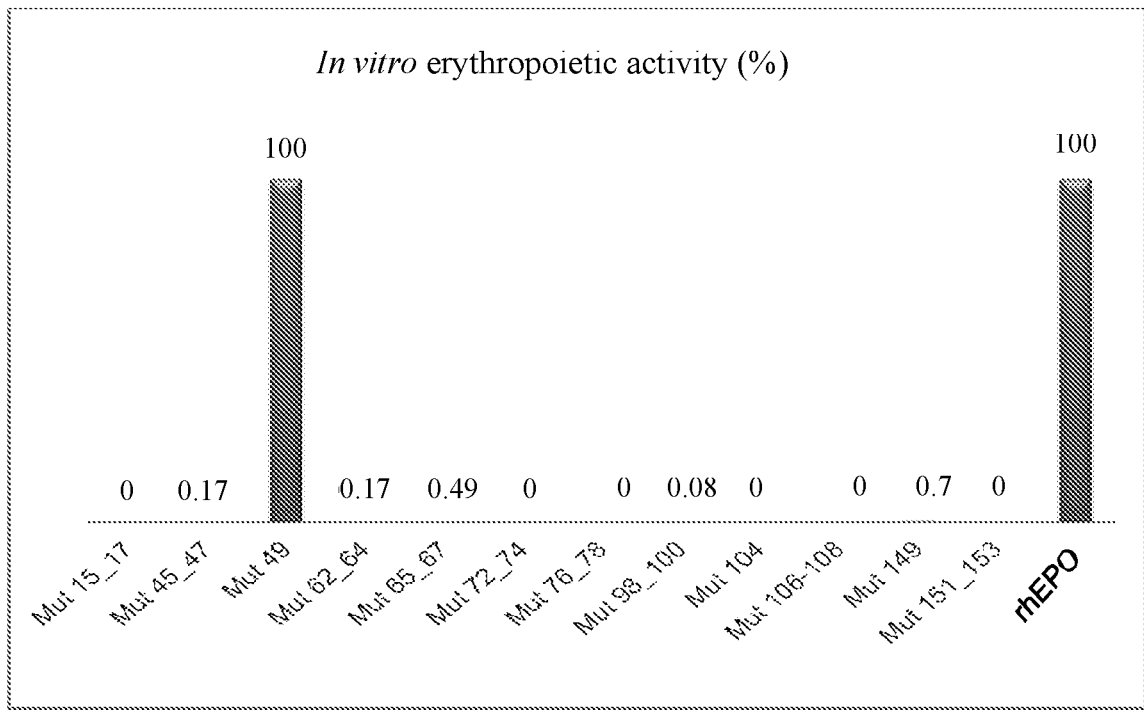
Figure 12B:
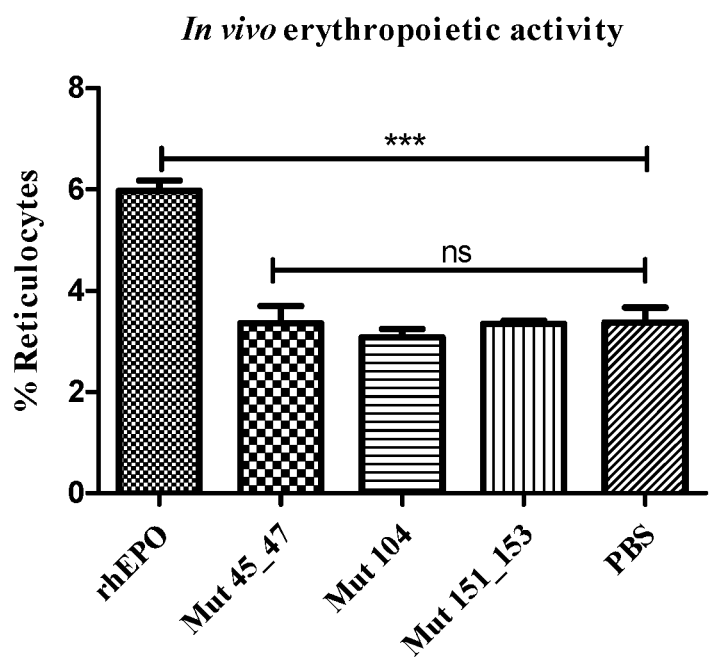

FIG. 12-a-. Comparison of the specific erythropoietic biological activity evaluated in vitro for hEPO muteins.

FIG. 12-b-. Evaluation of in vivo erythropoietic activity for hEPO muteins. The in vivo erythropoietic activity of hEPO muteins (Mut) was evaluated in normocytemic mice (n=4), that were treated with the same rhEPO mass or hEPO mut, as appropriate, or with PBS as control. After treatment, the reticulocytes percentage was quantified for each treatment. ***p≤0.001 and ns (not significant) represent the degree of statistical significance after ANOVA test y post-ANOVA Tukey test (n=4).

Figure 13:
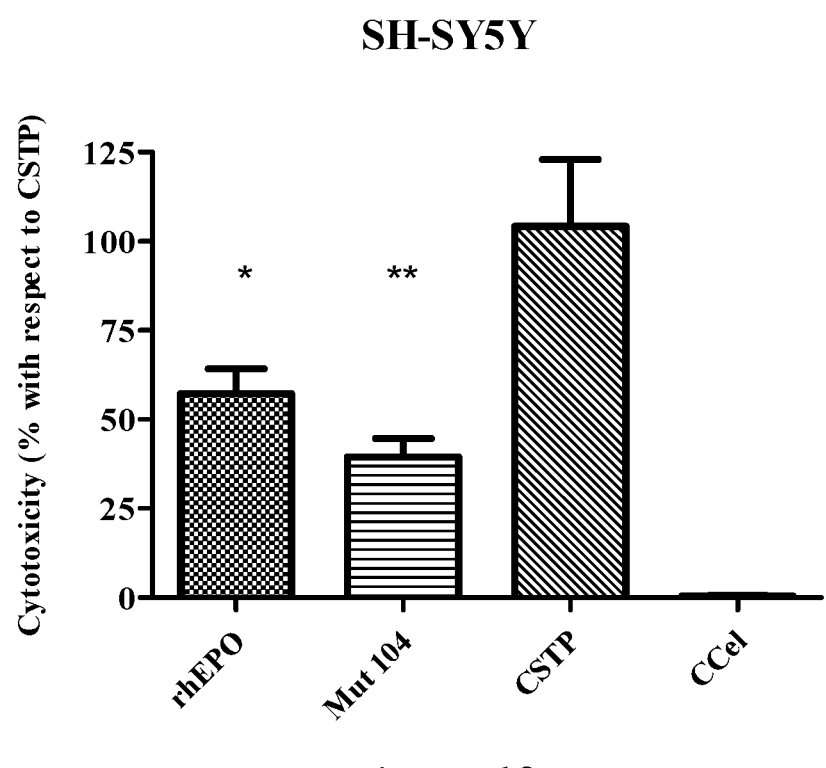

FIG. 13. Cyto/neuroprotective activity of rhEPO and Mut 104, using cell cultures of neuronal origin SH-SY5Y. CSTP: control of staurosporine (STP) addition, Ccel: cell control (without the addition of STP or muteins). *p≤0.05 and **p≤0.01 represent the degree of statistical significance after ANOVA test y post-ANOVA Dunnet test (n=3).

Figure 14:
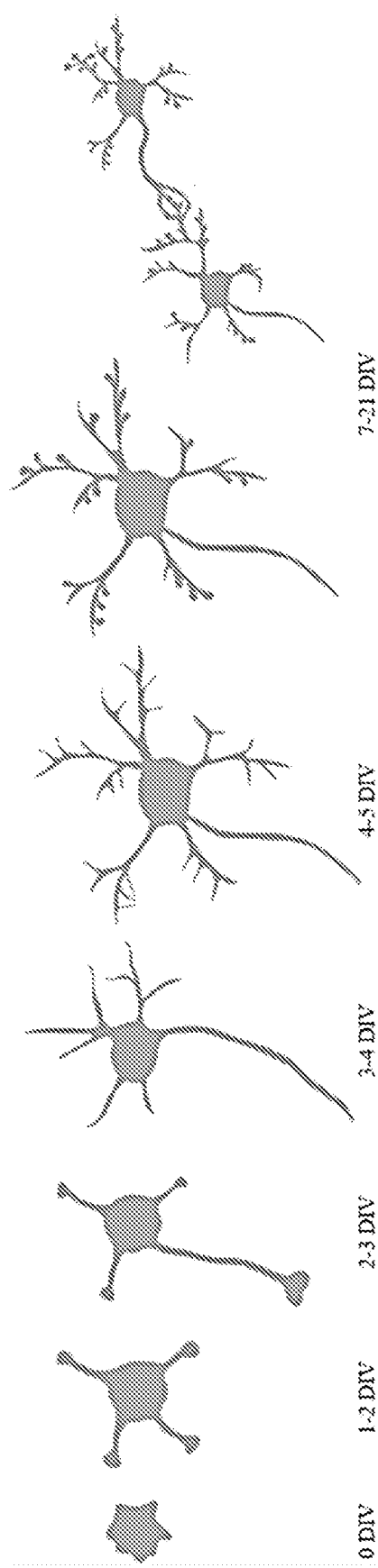

FIG. 14. Representative diagram of neuronal development in primary cultures of hippocampal neurons.

Figure 15A:
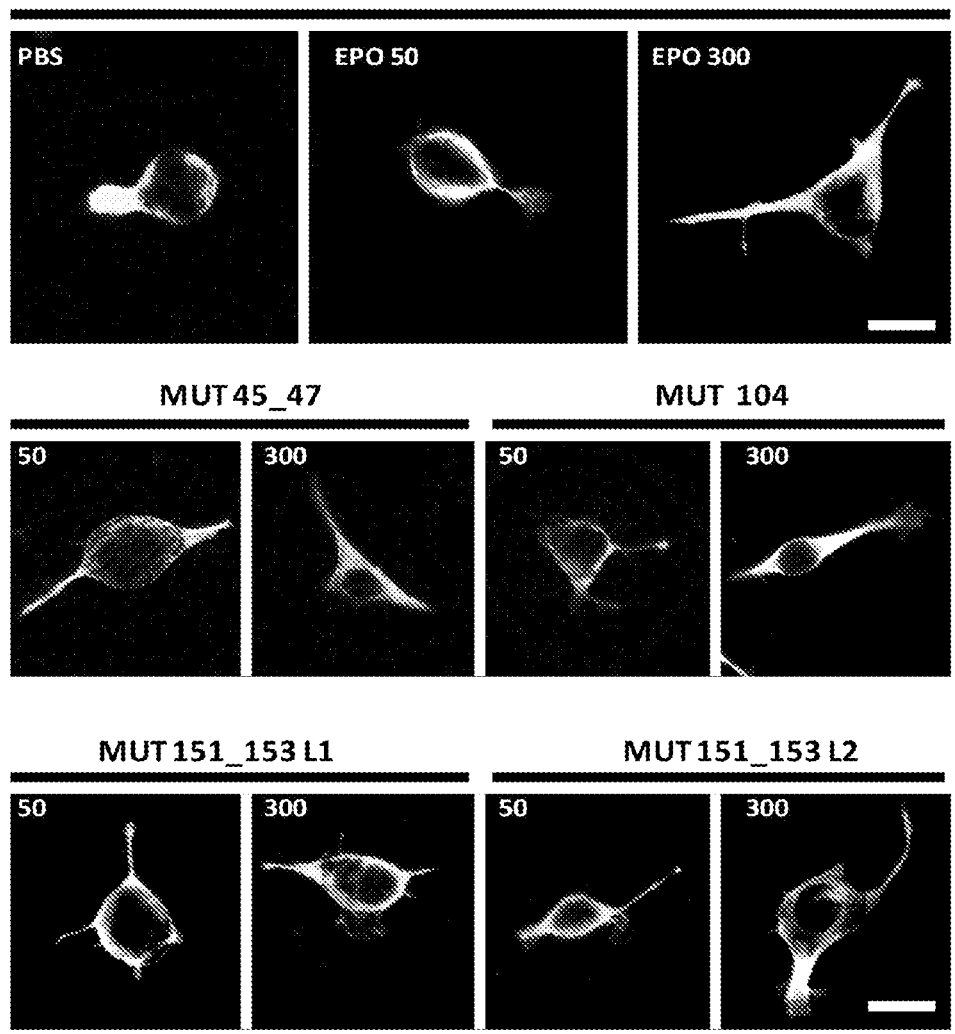
Figure 15B:
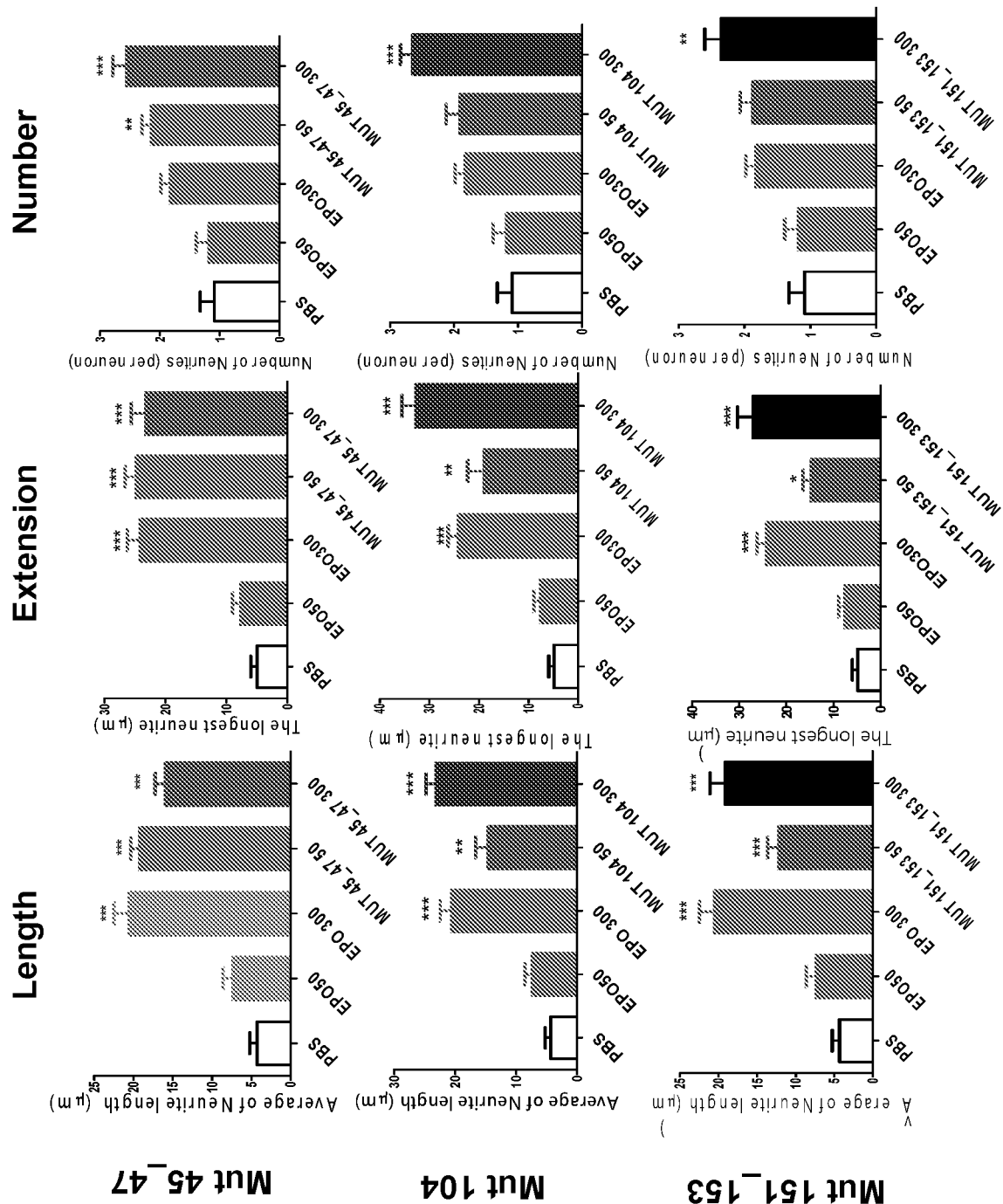

FIG. 15. Evaluation of neurites formation through murine N2a cells. (a) Representative images of each of the analyzed groups. (b) Graphic representation obtained from the evaluation of the following parameters of the neurites: average length, extension of the longest neurite and average number of neurites per neuron. *p≤0.05 and **p≤0.01 represent the degree of statistical significance after ANOVA test y post-ANOVA Bonferroni test (n=3).

Figure 16:
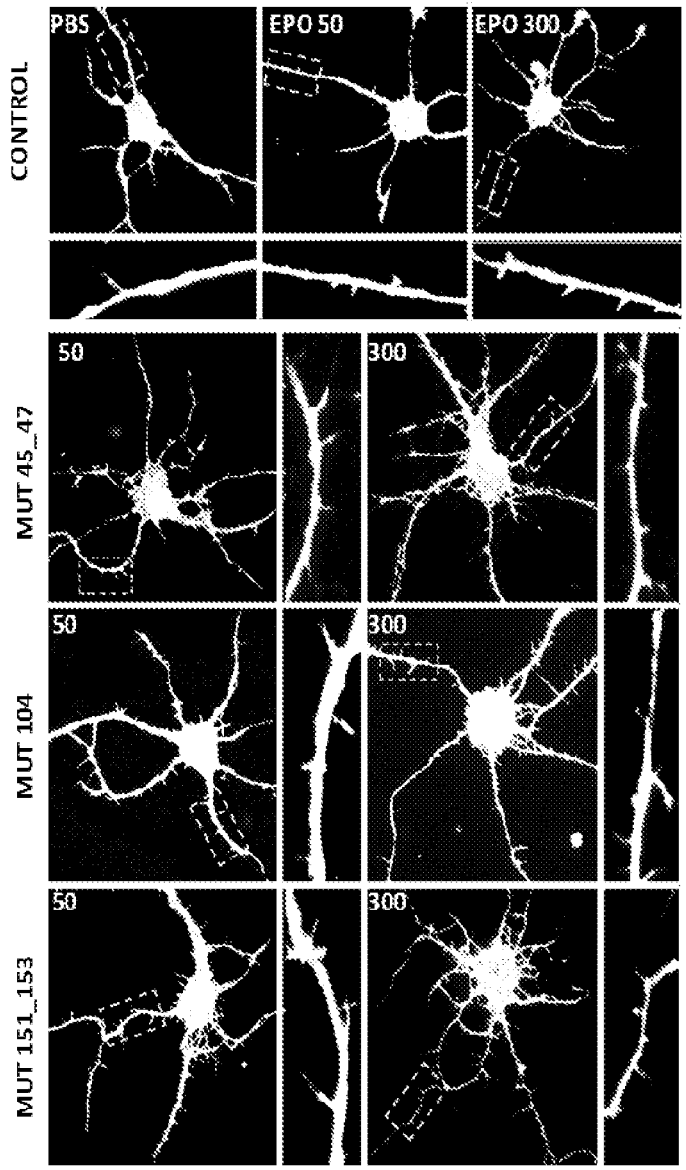
Figure 16:
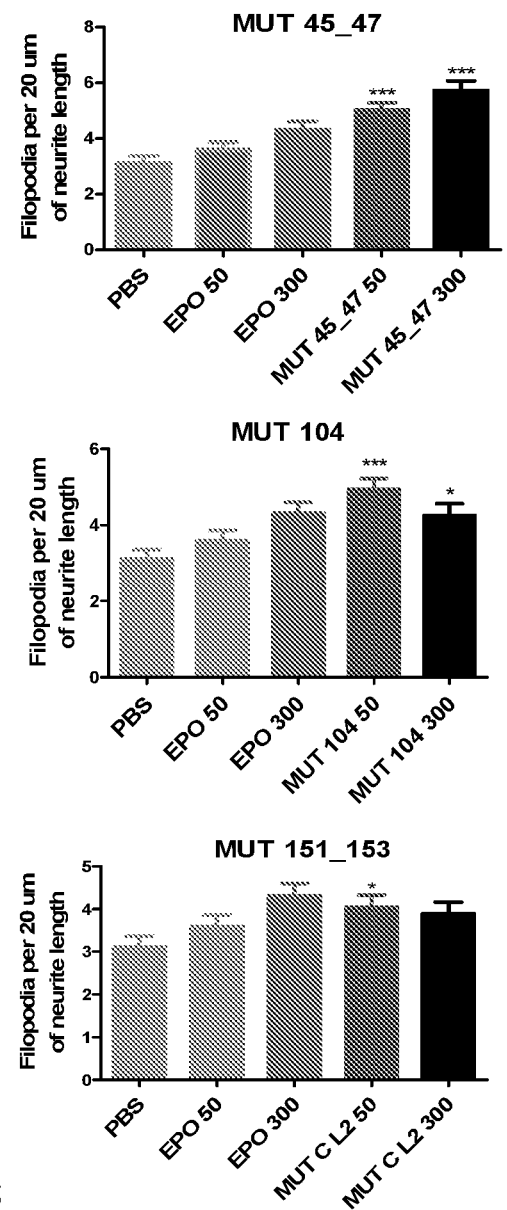

FIG. 16. Evaluation of filopodia density using primary cultures of hippocampal neurons from rat embryos. *p≤0.05 and **p≤0.01 represent the degree of statistical significance after ANOVA test y post-ANOVA Bonferroni test (n=3).

Figure 17:
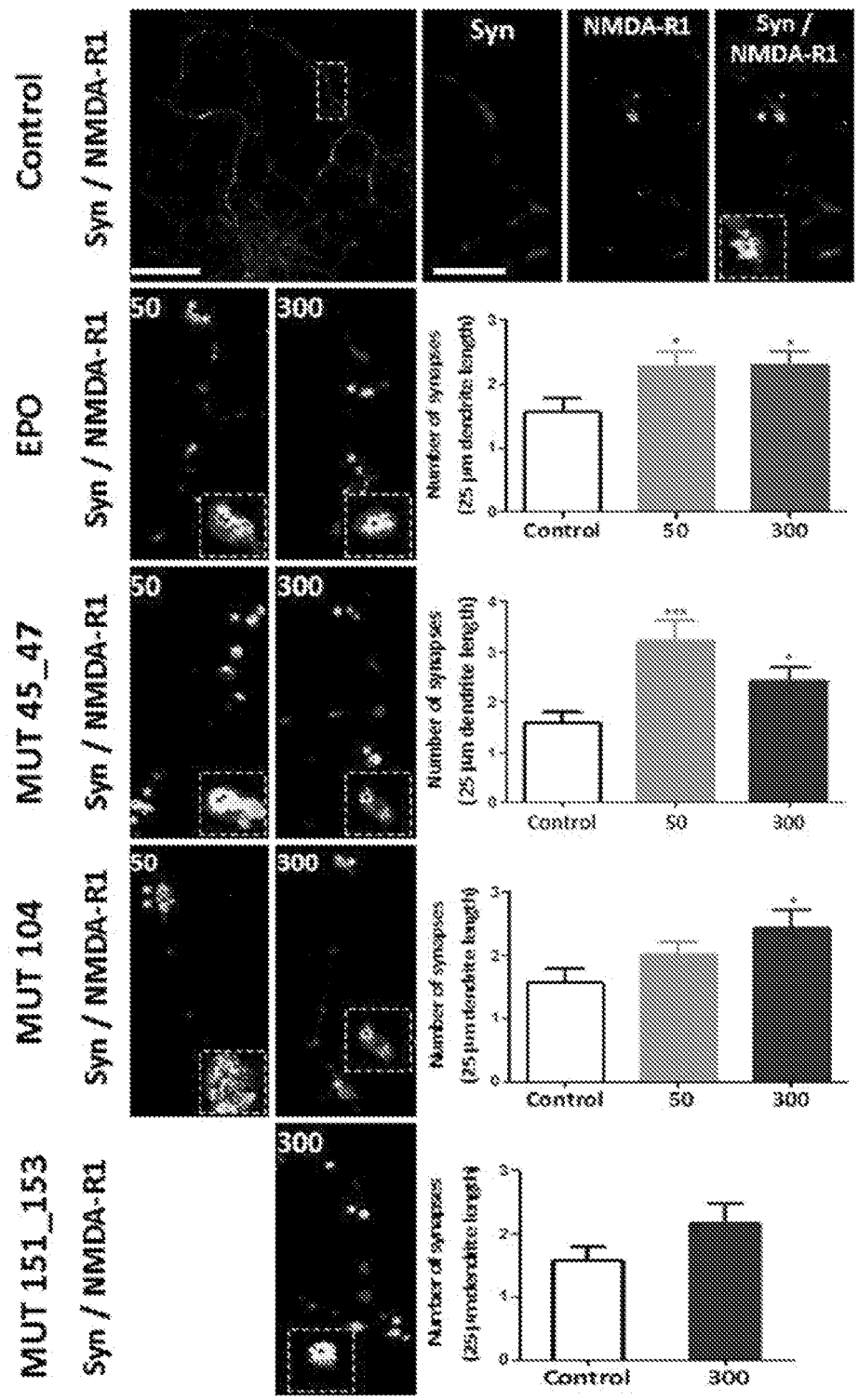

FIG. 17. Evaluation of synapse formation using primary cultures of hippocampal neurons from rat embryos. *p≤0.05 ***p≤0.001 represent the degree of statistical significance after ANOVA test y post-ANOVA Bonferroni test (n=3).

Figure 18:
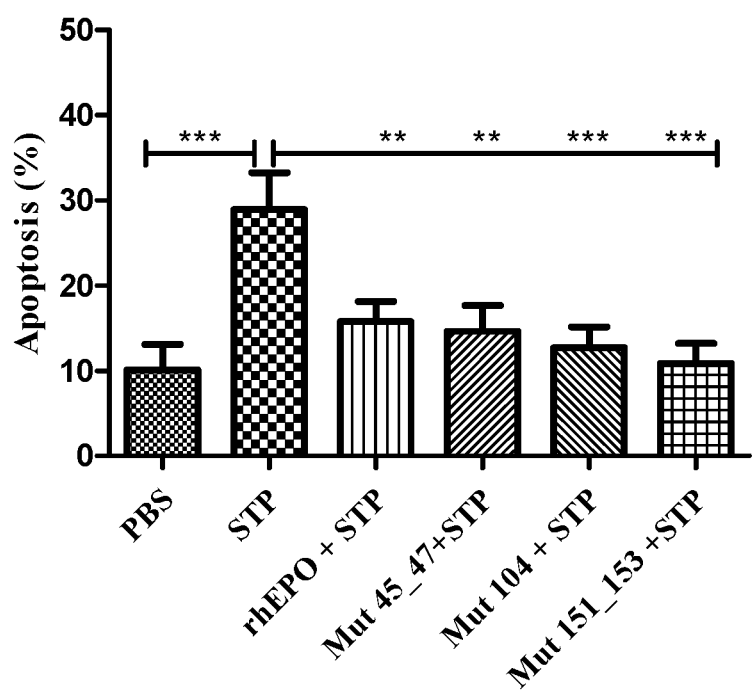

FIG. 18. Evaluation of the neuroprotective biological activity of hEPO muteins on primary neural cultures of 11 days of in vitro (DIV) culture. The in vitro neuroprotective activity of hEPO muteins (Mut) was evaluated in primary cultures of hippocampal neurons of Sprague-Dawley rats of 11 DIV. Cultures were treated with equal mass of rhEPO or muteins, as appropriate, or with PBS as control. Then, apoptosis was induced by incubation with staurosporine (STP). An immunofluorescence was performed with Hoescht and Phalloidin-FITC reagents to analyze the percentage of apoptotic nuclei. *p≤0.001, p≤0.01 and ns (not significant) represent the degree of statistical significance after ANOVA test y post-ANOVA Bonferroni test.

DETAILED DESCRIPTION OF THE INVENTION

As it was mentioned in the state of the art, the aim was to try to design different strategies to decrease the erythropoietic activity of the cytokine, maintaining its neuroprotective and neurotrophic potential, which have been based on the application of chemical modifications on the molecule or the manipulation of its glycosidic content. However, the state of the art has not described the use of glycosylation as a blocking mechanism of the molecular portion involved in the interaction that is responsible for the erythropoiesis.

Therefore, this invention provides a new modified erythropoietin that solves the problems mentioned in the state of the art by simultaneously achieving:

An inhibition of hEPO hematopoietic function in patients who require treatment related to neuroprotection and where erythropoiesis becomes an adverse effect.

An extension of hEPO half-life in order to improve in vivo biological activity, and decrease the number of doses to be administered.

Thus, this invention includes the use of hyperglycosylated muteins derived from hEPO for the preparation of a pharmaceutical composition intended for the prevention or treatment of a disease or genetic predisposition to suffer such a disease, in which neuroplasticity and/or neuroprotection have a beneficial effect. This invention could be administered to patients with neurodegenerative diseases such as Alzheimer's disease (AD), Parkinson's disease (PD), amyotrophic lateral sclerosis (ALS), among others; to patients suffering from motor neurons diseases, such as Huntington's disease, spinocerebellar atrophies, Creutzfeld-Jakob disease, among others; disabling diseases such as depression or schizophrenia; developmental diseases such as Down syndrome, as well as people who have suffered nerve tissue damage from cerebrovascular accidents or cranioencephalic trauma.

The term "mutein" in this document refers to a protein that has been modified by a site-directed mutation that includes the replacement of 1 or 2 of its amino acid residues in order to introduce a consensus and potential site for N-glycosylation.

The generation or addition of consensus sites for N-glycosylation includes the mutation of an amino acid at a site or region of the molecule of interest. For a cell to perform the addition of glycans, it is necessary for an Asn-Xaa-Ser/Thr site to be present, where Xaa can be any amino acid other than Pro. For this, if an Asn residue is present in the site where an N-glycosylation site wants to be added, the amino acid in position+2 (with respect to Asn) is mutated to Thr, which has greater efficiency if compared to Ser so that the Asn residue is occupied by glycans. In a different way, if the site to be modified has an amino acid in position+2 evidencing the presence of Ser or Thr, this amino acid is mutated to Asn. That is to say, there are conservative changes at all times.

This invention describes a human erythropoietin that has a modification of the amino acid structure that allows for the following achievements:

i. Preservation of amino acid residues that constitute essential sites for the molecular conformation or for the development of the neuroprotective/neuroplastic activity.

ii. Modification of the amino acids proposed in the abolition of hematopoietic activity.

iii. Generation of consensus sites for N-glycosylation.

12 hEPO muteins have been constructed. In these muteins, the modification of 1 or 2 amino acids was carried out to incorporate consensus sites for N-glycosylation in order to abolish the hematopoietic activity, preserve neuroprotective/neuroplastic activity and obtain mutants with a superior plasma half-life.

The assays carried out to obtain the molecules of this invention are detailed below. These assays are meant to exemplify the application and should be understood in their broadest sense, without limiting the scope of protection of this invention.

1. Design and Obtainment of hEPO-Derived Muteins that Abolish Erythropoietic Activity and Preserve Neuroprotective/Neuroplastic Action.

We designed 26 oligonucleotides: 2 of them to amplify the new complete EPO sequences, and the remaining 24 (forward and reverse oligonucleotides) to introduce the 12 point mutations.

According to the description provided in this invention, the modifications should be interpreted as the substitution of an amino acid in a given position by another amino acid in the same position. Therefore, and taking Mutation 1(Lys45→Asn45)+(Asn47→Thr47) as an example, it should be interpreted as the change of the lysine residue in position 45 for the asparagine residue in said position and the change of asparagine in position 47 for threonine.

The strategy implemented to generate hEPO muteins by site-directed mutagenesis is summarized in the scheme shown in FIG. 1.

Using hEPO DNA as template, oligonucleotides for each mutant and oligonucleotides pMATEPOF (AGGCCAGTCTTGTGCTCCAGGTACCG) which bind complementary to the ends of the hEPO sequence, a first PCR was performed to introduce each of the aforementioned mutations. 24 fragments were obtained, corresponding to the 12 hEPO muteins. The nucleotide and amino acid sequences of said 12 synthesized hEPO muteins (muteins) are:

```
MUTEIN 15-17 (Tyr15 →Asn15) + (Leu17 →Thr17)
Primers were:
Mut15_17F: GTGCTGGAAAGAAACCTGACGGAAGCCAAA

MUT15_17R: TTTGGCTTCCGTCAGGTTTCTTTCCAGCAC

NUCLEOTIDES SEQUENCE OF MUTEIN 15-17
                                              (SEQ ID No. 1)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

AAACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF MUTEIN 15-17
                                              (SEQ ID No. 2)
MGVHECPAWLWLLLSLLSLPLGLPVLGAPPRLICDSRVLERNLLEAKEAENITTGCAEHCS

LNENITVPDTKVNFYAWKRMEVGQQAVEVWQGLALLSEAVLRGQALLVNSSQPWEPLQLHV

DKAVSGLRSLTTLLRALGAQKEAISPPDAASAAPLRTITADTFRKLFRVYSNFLRGKLKLY

TGEACRTGDR

MUTEIN 45-47 (Lys45 →Asn45) + (Asn47 →Thr47)
Primers were:
Mut45_47F: CCCGACACCAACGTGACCTTCTACGCC Mut45_47R: GGCGTGAAGGTCACGTTGGTGTCGGG NUCLEOTIDES SEQUENCE OF MUTEIN 45-47
                                              (SEQ ID No. 3)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAACGTGACCTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA
```

```
AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA
```

AMINO ACIDS SEQUENCE OF MUTEIN 45-47
(SEQ ID No. 4)
```
MGVHECPAWLWLLLSLLSLPLGLPVLGAPPRLICDSRVLERYLLEAKEAENITTGCAEHCS

LNENITVPDTNVTFYAWKRMEVGQQAVEVWQGLALLSEAVLRGQALLVNSSQPWEPLQLHV

DKAVSGLRSLTTLLRALGAQKEAISPPDAASAAPLRTITADTFRKLFRVYSNFLRGKLKLY

TGEACRTGDR
```

MUTEIN 49 (Tyr49 →4Thr49)
Primers were:
Mut49F: AAAGTGAACTTCACCGCCTGGAAGCGG

Mut49R: CCGCTTCCAGGCGGTGAAGTTCACTTT

NUCLEOTIDES SEQUENCE OF MUTEIN 49
(SEQ ID No. 5)
```
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCACCGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA
```

AMINO ACIDS SEQUENCE OF MUTEIN 49
(SEQ ID No. 6)
```
MGVHECPAWLWLLLSLLSLPLGLPVLGAPPRLICDSRVLERYLLEAKEAENITTGCAEHCS

LNENITVPDTKVNFTAWKRMEVGQQAVEVWQGLALLSEAVLRGQALLVNSSQPWEPLQLHV

DKAVSGLRSLTTLLRALGAQKEAISPPDAASAAPLRTITADTFRKLFRVYSNFLRGKLKLY

TGEACRTGDR
```

MUTEIN 62-64 (Glu62 →Asn62) + (Trp64 →Thr64)
Primers were:
Mut62_64F: CAGGCTGTGAACGTGACGCAGGGACTG

MUT62 64R: CAGTCCCTGCGTCACGTTCACAGCCTG

NUCLEOTIDES SEQUENCE OF MUTEIN 62-64
(SEQ ID No. 7)
```
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGAACGTGACGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA
```

AMINO ACIDS SEQUENCE OF MUTEIN 62-64
(SEQ ID No. 8)
MGVHECPAWLWLLLSLLSLPLGLPVLGAPPRLICDSRVLERYLLEAKEAENITTGCAEHCS

LNENITVPDTKVNFYAWKRMEVGQQAVNVTQGLALLSEAVLRGQALLVNSSQPWEPLQLHV

DKAVSGLRSLTTLLLRALGAQKEAISPPDAASAAPLRTITADTFRKLFRVYSNFLRGKLKLY

TGEACRTGDR

MUTEIN 65-67 (Gln65 →Asn65) + (Leu67 →Thr67)
Primers were:
Mut65_67F: GAAGTGTGGAACGGAACGGCTCTGCTG

MUT65_67R: CAGCAGAGCCGTTCCGTTCCACACTTC

NUCLEOTIDES SEQUENCE OF MUTEIN 65-67
(SEQ ID No. 9)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGAACGGAACGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF MUTEIN 65-67
(SEQ ID No. 10)
MGVHECPAWLWLLLSLLSLPLGLPVLGAPPRLICDSRVLERYLLEAKEAENITTGCAEHCS

LNENITVPDTKVNFYAWKRMEVGQQAVEVWNGTALLSEAVLRGQALLVNSSQPWEPLQLHV

DKAVSGLRSLTTLLLRALGAQKEAISPPDAASAAPLRTITADTFRKLFRVYSNFLRGKLKLY

TGEACRTGDR

MUTEIN 72-74 (Glu72 →Asn72) + (Val74 →Thr74)
Primers were:
Mut72_74F: CTGCTGAGCAACGCTACGCTGAGAGGA

MUT72_74R: TCCTCTCAGCGTAGCGTTGCTCAGCAG

NUCLEOTIDES SEQUENCE OF MUTEIN 72-74
(SEQ ID No. 11)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCAACGCTACGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF MUTEIN 72-74
(SEQ ID No. 12)
MGVHECPAWLWLLLSLLSLPLGLPVLGAPPRLICDSRVLERYLLEAKEAENITTGCAEHCS

-continued
LNENITVPDTKVNFYAWKRMEVGQQAVEVWQGLALLSNATLRGQALLVNSSQPWEPLQLHV

DKAVSGLRSLTTLLLRALGAQKEAISPPDAASAAPLRTITADTFRKLFRVYSNFLRGKLKLY

TGEACRTGDR

MUTEIN 76-78 (Arg76 →Asn76) + (Gln78 →Thr78)
Primers were:
Mtt76_78F: GCTGTGCTGAACGGAACGGCCCTGCTC

MUT76_78R: GAGCAGGGCCGTTCCGTTCAGCACAGC

NUCLEOTIDES SEQUENCE OF MUTEIN 76-78
(SEQ ID No. 13)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAACGGAACGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF MUTEIN 76-78
(SEQ ID No. 14)
MGVHECPAWLWLLLSLLSLPLGLPVLGAPPRLICDSRVLERYLLEAKEAENITTGCAEHCS

LNENITVPDTKVNFYAWKRMEVGQQAVEVWQGLALLSEAVLNGTALLVNSSQPWEPLQLHV

DKAVSGLRSLTILLRALGAQKEAISPPDAASAAPLRTITADTERKLERVYSNFLRGKLKLY

TGEACRTGDR

MUTEIN 98-100 (Ala98 →Asn98) + (Ser100 →Thr100)
Primers were:
Mut98_100F: GTGGACAAGAATGTGACCGGCCTGAGATCC

MUT98_100R: GGATCTCAGGCCGGTCACATTCTTGTCCAC

NUCLEOTIDES SEQUENCE OF MUTEIN 98-100
(SEQ ID No. 15)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGAATGTGACCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF MUTEIN 98-100
(SEQ ID No. 16)
MGVHECPAWLWLLLSLLSLPLGLPVLGAPPRLICDSRVLERYLLEAKEAENITTGCAEHCS

LNENITVPDTKVNFYAWKRMEVGQQAVEVWQGLALLSEAVLRGQALLVNSSQPWEPLQLHV

DKNVTGLRSLTTLLLRALGAQKEAISPPDAASAAPLRTITADTFRKLFRVYSNFLRGKLKLY

TGEACRTGDR

MUTEIN 104 (Ser104 →Asn104)
Primers were:
Mut104F: TCCGGCCTGAGAAACCTGACCACCCTG

MUT104R: CAGGGTGGTCAGGTTTCTCAGGCCGGA

NUCLEOTIDES SEQUENCE OF MUTEIN 104
(SEQ ID No. 17)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGAAACCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF MUTEIN 104
(SEQ ID No. 18)
MGVHECPAWLWLLLSLLSLPLGLPVLGAPPRLICDSRVLERYLLEAKEAENITTGCAEHCS

LNENITVPDTKVNFYAWKRMEVGQQAVEVWQGLALLSEAVLRGQALLVNSSQPWEPLQLHV

DKAVSGLRNLTTLLRALGAQKEAISPPDAASAAPLRTITADTFRKLFRVYSNFLRGKLKLY

TGEACRTGDR

MUTEIN 106-108 (Thr106 →Asn106) + (Leu108 →Thr108)
Primers were:
Mtt106_108F: AGATCCCTGAACACCACGCTGAGAGCA

MUT106_108R: TGCTCTCAGCGTGGTGTTCAGGGATCT

NUCLEOTIDES SEQUENCE OF MUTEIN 106-108
(SEQ ID No. 19)
ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGAACACCACGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF MUTEIN 106-108
(SEQ ID No. 20)
MGVHECPAWLWLLLSLLSLPLGLPVLGAPPRLICDSRVLERYLLEAKEAENITTGCAEHCS

LNENITVPDTKVNFYAWKRMEVGQQAVEVWQGLALLSEAVLRGQALLVNSSQPWEPLQLHV

DKAVSGLRSLNTTLRALGAQKEAISPPDAASAAPLRTITADTFRKLFRVYSNFLRGKLKLY

TGEACRTGDR

MUTEIN 149 (Leu149 →Thr149)
Primers were:
Mut149F: TACTCCAACTTCACGCGGGGCAAGCTG

MUT149R: CAGCTTGCCCCGCGTGAAGTTGGAGTA

NUCLEOTIDES SEQUENCE OF MUTEIN 149

(SEQ ID No. 21)

ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCACGCGGGGCAAGCTGAAGCTGTAC

ACCGGCGAGGCTTGCCGGACCGGCGACAGA

AMINO ACIDS SEQUENCE OF MUTEIN 149

(SEQ ID No. 22)

MGVHECPAWLWLLLSLLSLPLGLPVLGAPPRLICDSRVLERYLLEAKEAENITTGCAEHCS

LNENITVPDTKVNFYAWKRMEVGQQAVEVWQGLALLSEAVLRGQALLVNSSQPWEPLQLHV

DKAVSGLRSLTTLLRALGAQKEAISPPDAASAAPLRTITADTFRKLFRVYSNFTRGKLKLY

TGEACRTGDR

MUTEIN 151-153 (Gly151 →Asn151) + (Leu153 →Thr153)
Primers were:
Mut151 153F: AACTTCCTGCGGAACAAGACGAAGCTGTAC

MUT151 153R: GTACAGCTTCGTCTTGTTCCGCAGGAAGTT

NUCLEOTIDES SEQUENCE OF MUTEIN 151-153

(SEQ ID No. 23)

ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGAACAAGACGAAGCTGTAC

ACCGGCGAGGCTTGCCGGACCGGCGACAGA

AMINO ACIDS SEQUENCE OF MUTEIN 151-153

(SEQ ID No. 24)

MGVHECPAWLWLLLSLLSLPLGLPVLGAPPRLICDSRVLERYLLEAKEAENITTGCAEHCS

LNENITVPDTKVNFYAWKRMEVGQQAVEVWQGLALLSEAVLRGQALLVNSSQPWEPLQLHV

DKAVSGLRSLTTLLRALGAQKEAISPPDAASAAPLRTITADTFRKLFRVYSNFLRNKTKLY

TGEACRTGDR

HUMAN EPO SEQUENCE
NUCLEOTIDES SEQUENCE OF HUMAN EPO (SEQ ID No. 25)

ATGGGCGTGCACGAATGTCCTGCTTGGCTGTGGCTGCTGCTGTCCCTGCTGTCTCTGCCTC

TGGGACTGCCTGTGCTGGGCGCTCCTCCTAGACTGATCTGCGACTCCCGGGTGCTGGAAAG

ATACCTGCTGGAAGCCAAAGAGGCCGAGAACATCACCACCGGCTGCGCCGAGCACTGCTCC

-continued

```
CTGAACGAGAATATCACCGTGCCCGACACCAAAGTGAACTTCTACGCCTGGAAGCGGATGG

AAGTGGGCCAGCAGGCTGTGGAAGTGTGGCAGGGACTGGCTCTGCTGAGCGAGGCTGTGCT

GAGAGGACAGGCCCTGCTCGTGAACTCCTCCCAGCCTTGGGAACCCCTGCAGCTGCACGTG

GACAAGGCTGTGTCCGGCCTGAGATCCCTGACCACCCTGCTGAGAGCACTGGGAGCCCAGA

AAGAGGCCATCTCTCCACCTGACGCCGCCTCTGCTGCTCCTCTGAGAACCATCACCGCCGA

CACCTTCAGAAAGCTGTTCCGGGTGTACTCCAACTTCCTGCGGGGCAAGCTGAAGCTGTAC

ACCGGCGAGGCTTGCCGGACCGGCGACAGA

AMINO ACIDS SEQUENCE OF HUMAN EPO
                                              (SEQ ID No. 26)
MGVHECPAWLWLLLSLLSLPLGLPVLGAPPRLICDSRVLERYLLEAKEAENITTGCAEHCS

LNENITVPDTKVNFYAWKRMEVGQQAVEVWQGLALLSEAVLRGQALLVNSSQPWEPLQLHV

DKAVSGLRSLTTLLRALGAQKEAISPPDAASAAPLRTITADTFRKLFRVYSNFLRGKLKLY

TGEACRTGDR
```

Figure 2B:
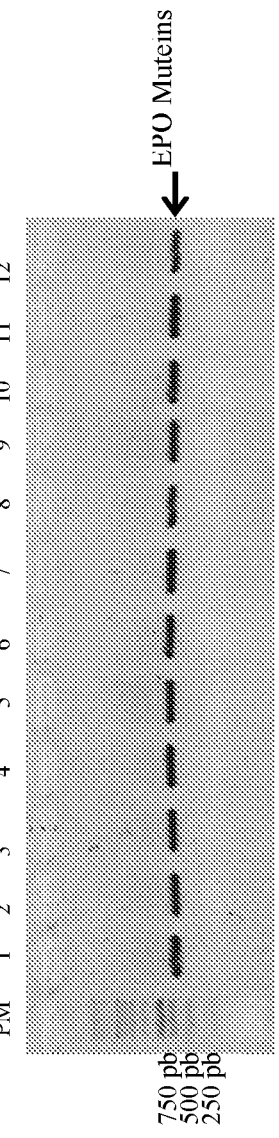

These are shown in FIG. 2a. These fragments were used as template to perform a second PCR, this time using only the oligonucleotides that bind to hEPO ends in order to obtain the sequence of the 12 mutants (FIG. 2b). After PCR reactions, the products corresponding to the 12 hEPO muteins were digested with the restriction enzymes XbaI/SalI, which flank hEPO molecule, to be cloned in pLV-PLK vector, digested with the same restriction enzymes. TOP TEN bacteria were transformed and selected by ampicillin. 3-4 colonies of each hEPO mutein were amplified in liquid medium to perform mini-preparations of plasmid DNA. Then, we confirmed the presence of the insert by restriction enzymes digestion of the sites present in the hEPO sequence and absent in the vector sequence. At last, plasmid DNA mini-preparations were sequenced to confirm the insertion of the mutations carried out on the hEPO molecule.

2. In Silico Analysis of hEPO Muteins Potential Antigenicity

IEDB database (Immune Epitope Database and Analysis Resources) was used to perform an in silico analysis to compare the potential antigenicity of hEPO muteins and the potential antigenicity of the unmodified molecule. For all of them, a prediction of T epitopes—recognized in Class II Major Histocompatibility Complex (MHC II)—was performed by analyzing the 8 most representative alleles worldwide (HUMAN, HLA-DR: DRB1*01.01, DRB1*03.01, DRB1*04.01, DRB1*07.01, DRB1*08.01, DRB1*11.01, DRB1*13.01, DRB1*15.01). An antigenicity score was obtained for each hEPO variant, and each was compared to the score obtained for hEPO. The degree of potential antigenicity for each of them is schematically summarized in FIG. 3. Thus, two muteins with the same degree of antigenicity as hEPO were observed (Mut98_100, Mut151_153), two muteins potentially more antigenic (Mut72_74 and Mut62_64) and, finally, 8 muteins potentially less antigenic (Mut45_47, Mut49, Mut15_17, Mut65_67, Mut149, Mut76_78, Mut104, and Mut106_108), and these last two were the ones with less antigenicity.

3. Obtaining Cell Lines that Produce the Mentioned Muteins

Lentiviral particles were assembled to subsequently transduce CHO.K1 cells. For this reason, HEK 293 T/17 cells (packaging cells) were co-transfected with 4 vectors to generate the corresponding lentiviral particles for each of the 12 muteins. The 4 vectors used were: pREV (which induces the nuclear export of the transfer vector and its packaging), pVSVG (which encodes VSV envelope G protein, necessary for the entry of the viral particle into the cell, with a broad tropism), pMDL (which encodes matrix and capsid proteins—capable of packaging the expression vector—, protease, reverse transcriptase and integrase—required for cleavage of structural elements and for integration into the cell genome) and the transfer vector pLV-PLK-Mut X in which all viral genes have been removed and replaced by the genes of interest corresponding to hEPO muteins of this invention. Two days after transfection of HEK 293T/17 cells, supernatants from each of the cells containing mut X lentiviral particles were harvested, which were used to transduce CHO.K1 cells. The 12 CHO.K1 mut X hEPO lines were obtained. After 72 hrs, the supernatants were harvested and preserved for later characterization. Likewise, in order to generate stable recombinant cell lines, they were pressed with increasing amounts of puromycin antibiotic, so as to select those cells that incorporated the transgene. Pressed cell lines were amplified and cryopreserved in a cryogenic mixture (90% (v/v) FBS, 10% (v/v) DMSO), and they were stored in liquid nitrogen tanks.

Initially, through the Sandwich ELISA technique and antibodies specific for the hEPO molecule, concentration was determined using the culture of cell lines obtained by transduction. A monoclonal antibody was used as capture and rabbit polyclonal antibodies were used for detection (both types of antibodies were developed in our laboratory). The concentrations obtained (shown in Table I) were considered adequate for the continuity of the studies.

Furthermore, culture supernatants were analyzed by Western Blot technique, using polyclonal antibodies to detect all hEPO muteins. This methodology allowed us to visualize that the muteins presented greater molecular mass when compared to the unmodified hEPO, which coincides with the insertion of new N-glycosylation sites in the molecular structure (FIG. 4).

Likewise, an isoelectric focusing analysis and then a Western Blot analysis were performed to study the number of glycoisoforms in each of the hEPO muteins expressed in CHO.K1 cell culture supernatants. The number of isoforms obtained in 11 of the 12 muteins evaluated was higher than that of the unmodified hEPO. The range of isoforms ranged from 8 to 16 isoforms when compared to the 7 isoforms that were observed in the culture supernatant of the unmodified hEPO.

The present invention provides hEPO muteins that have little or no erythropoietic activity to avoid the side effects produced by the cytokine when used as a potential neuroprotective/neuroplastic candidate. For this reason, the aforementioned in vitro activity was studied, using TF-1 cells whose proliferation depends on the presence of hEPO. In order to measure erythropoietic activity, the proliferation of these cells was evaluated after 96 hrs of stimulation with a hEPO standard with a well-known biological activity. All developed hEPO muteins successfully exhibited reduced or no erythropoietic activity when compared to the commercial hEPO standard and the unmodified hEPO molecule, except for Mut49 which maintained its erythropoietic activity. Results are summarized in Table I.

TABLE I

Characterization of hEPO muteins.
Concentration quantification in culture supernatants by Sandwich ELISA, evaluation of the number of isoforms measured by isoelectric focusing and determination of in vitro biological activity expressed as a percentage with respect to the unmodified molecule.

| Mutein | Concentration (µg/ml) | No. of isoforms | Erythropoietic activity (in vitro) (%) |
|---|---|---|---|
| rhEPO | — | 7 | 100 |
| Mut15_17 | 2.7 | 8 | NDA |
| Mut45_47 | 12.6 | 12-13 | 0.17 |
| Mut49 | 6.4 | 14 | 100 |
| Mut62_64 | 17.2 | 10 | 0.17 |
| Mut65_67 | 32.0 | 12 | 0.49 |
| Mut72_74 | 23.3 | 14 | 0.42 |
| Mut76_78 | 51.0 | 5-6 | NDA |
| Mut98-100 | 19.0 | 13 | 0.08 |
| Mut104 | 15.9 | 16 | NDA |
| Mut106-108 | 16.5 | 12 | NDA |
| Mut149 | 24.3 | 10 | 0.07 |
| Mut151_153 | 3.7 | 9 | NDA |

NDA: non-detectable activity;
rhEPO: recombinant human erythropoietin;
Mut: mutein.

The present invention provides hEPO muteins containing sites susceptible to N-glycosylation at positions that do not abolish the cytoprotective biological activity but do abolish the hematopoietic activity. They were expressed in CHO.K1 cell culture supernatants and subsequently characterized. All of them showed a higher degree of glycosylation, achieving the objective of including an additional site for N-glycosylation that allows to increase their plasma half-life. Likewise, it was confirmed that the modifications made to the molecule had an effect on the hematopoietic biological activity, canceling it in most of the muteins or decreasing it drastically in the rest.

4. Purification of hEPO-Derived Muteins by Immunoaffinity Chromatography

A purification procedure for the muteins of the present invention is presented below. For a better understanding of this procedure, the following muteins are presented as an example: Mut 45_47, Mut 104, Mut 151_153, through a scheme of immunoaffinity (IA) purification. Initially, we simulated a process equivalent to the one that occurs in an IA matrix with the aim of establishing the most favorable condition to elute each of the hyperglycosylated hEPO muteins captured by an anti-rhEPO monoclonal antibody which was developed for this purpose in our laboratory (Protocol A). Based on the above, sandwich ELISA assays were performed to quantify the ratio of hEPO derivatives that remained bound to mAb 2B2 after the antigen-antibody complex was subjected to each elution condition. Likewise, we evaluated the effect of each eluent solution on the antibody in order to determine whether they would affect the ability to bind to hEPO muteins in view of the future reuse procedures of IA matrixes (Protocol B).

The eluent capacity of the following solutions was evaluated:
1. Glycine 0.1 M pH 2
2. Glycine 0.15 M pH 2.5
3. Acetic acid 0.2 M, NaCl 0.15 M pH 2.5
4. Glycine 0.15 M pH 3
5. Citric acid 0.1 M pH 3
6. Acetic acid 0.2 M, NaCl 0.15 M pH 3
7. Glycine 0.15 M pH 3.5
8. Sodium acetate 0.1 M pH 4
9. Sodium acetate 0.1 M/Dioxane 10% (v/v) pH 4
10. Sodium acetate 0.1 M pH 5
11. Sodium phosphate 0.1 M pH 6
12. Isopropyl alcohol 40% (v/v) in phosphate-buffered saline (PBS) pH 7
13. PBS pH 7
14. Ethanol 40% (v/v) in PBS pH 7
15. Dioxane 10% (v/v) in PBS pH 7
16. Ethylene glycol 40% (v/v) in PBS pH 7
17. Tris/HCl 0.1 M pH 8
18. Glycine 0.1 M pH 9
19. Glycine 0.1 M pH 10
20. Glycine 0.1 M pH 11
21. Sodium phosphate 0.1 M pH 11
22. Sodium phosphate 0.1 M pH 11.7

The absorbance values obtained for the antigen-antibody complex treated with PBS were considered as control, assuming 100% formation of the antigen-antibody complex; that is, without desorption of rhEPO or its muteins. For Protocol B, the absorbance values obtained for the antibody treated with PBS (prior to the formation of the Ag—Ac complex) were considered as control of the preservation of the antibody's binding capacity to the molecules under study. Therefore, the results obtained for the rest of the solutions tested were expressed relative to the controls evaluated with PBS (FIG. 5).

In all cases it was observed that the condition established by Glycine 0.1 M pH 2 had the highest capacity for desorption of the antigen when compared to the other solutions. However, the formation capacity of the aforementioned complex was reduced considerably after the previous treatment with it. Therefore, the use of such eluent in immunoaffinity chromatography is not convenient since it would affect the reuse of the chromatographic matrix.

On the other hand, this assay enabled the selection of two eluent solutions as candidates to be used in immunoaffinity chromatography (IAC): glycine 0.15 M pH 2.5 and acetic acid 0.2 M, NaCl 0.15 M pH 3. Both solutions were capable of dissociating Ag—Ac complexes, stripping the protein of interest (Table II) and, in addition, did not affect the ability of the antibody to bind the antigen after prior treatment with them.

TABLE II

Elution of hEPO muteins considering the selected eluent solutions.

| | Elution (%) | | |
|---|---|---|---|
| Solution | Mut 45 47 | Mut 104 | Mut 151 153 |
| (2) | 86 | 84 | 80 |
| (6) | 80 | 81 | 70 |

(2) Glycine 0.15M pH 2.5
(6) Acetic acid 0.2M NaCl 0.15M pH 3

The 2B2 mAb used in IA resins was previously purified by protein A affinity chromatography and dialyzed against a carbonate solution. Then, resin CNBr-Activated Sepharose4B was coupled. The coupling degree was calculated by measuring the concentration of immunoglobulins in the solution before and after the immobilization reaction, resulting in 96%. Thus, the theoretical capacity was rhEPO 481 μg per ml of gel.

FIG. 6 shows an examplary chromatographic profile of the purification of mutein Mut 104, using the glycine eluent solution 0.15 M pH 2.5.

Sandwich ELISA technique was used to evaluate in each chromatographic procedure the presence of the hEPO variant in the different fractions (flowthrough, washings, elution) in order to calculate the parameters that allow to analyze the process performance.

The results obtained for purifications are shown in Table III. Under dynamic conditions, some differences were observed regarding the efficiency in the recovery of the protein of interest when compared to the static conditions evaluated in plates. Elution with the pH 2.5 solution resulted in better recoveries for muteins Mut 104 and Mut 151_153, when compared to the pH 3 solution (54% vs. 19%, and 55% vs. 21%, respectively), while for the Mut 45_47 variant, greater recovery was obtained when eluting with the pH 3 solution (49% vs. 34%).

TABLE III

Purification parameters through immunoaffinity chromatography (IAC) of hEPO muteins.

| Sample | Eluent solution/Fraction | | rhEPO (μg/ml) | PT (μg/ml) | AE | FP | Recovery (%) |
|---|---|---|---|---|---|---|---|
| Mut 45_47 | Sol. I (pH 3) | Load | 18 | 433 | 0.04 | 1 | 100 |
| | | Elution | 8.9 | 17.7 | 0.5 | 12.1 | 49 |
| | Sol. II (pH 2.5) | Load | 17.3 | 611.8 | 0.03 | 1 | 100 |
| | | Elution | 5.9 | 5.7 | 1.04 | 37 | 34 |
| Mut 104 | Sol. I (pH 3) | Load | 23 | 315 | 0.07 | 1 | 100 |
| | | Elution | 14.4 | 21 | 0.69 | 10 | 19 |
| | Sol. II (pH 2.5) | Load | 20 | 245 | 0.08 | 1 | 100 |
| | | Elution | 13.2 | 3.6 | 3.71 | 46 | 54 |
| Mut 151_153 | Sol. I (pH 3) | Load | 3.2 | 510.4 | 0.01 | 1 | 100 |
| | | Elution | 3.5 | 6.4 | 0.56 | 89.1 | 21 |
| | Sol. II (pH 2.5) | Load | 1.7 | 491.5 | 0.004 | 1 | 100 |
| | | Elution | 3.9 | 14 | 0.31 | 89.7 | 55 |

Sol. I: Acetic acid 0.2M, NaCl 0.15M pH 3.0 and Sol. II: glycine 0.15M pH 2.5

When analyzing the different stages of the chromatographic process of mutein Mut 104 by SDS-PAGE followed by staining with Coomassie Brilliant Blue dye (FIG. 7), it can be observed that most of the contaminants present in the sample were not retained and were part of flowthrough and washings. Therefore, a high degree of purity was obtained as it is observed in lane 6 of the mentioned figure.

Although the IAC did not show high recovery of the protein of interest, it was the most suitable method for purification of hEPO muteins, as it enabled their purification 37-90 times with respect to the starting sample, with a high degree of purity and in a single chromatographic step.

The purity evaluation of the eluates corresponding to each hEPO mutein was performed by band densitometry (FIG. 8).

Prior to the electrophoretic run, samples were concentrated 75-80 times, using diafiltration cartridges with a 10 kDa cutoff point. The purity obtained was above 89% for all muteins (Table IV), which are characteristic values for an IA purification procedure.

TABLE IV

Purity degree of the eluates obtained from each immunoaffinity chromatography (IAC)

| | Muteins | | |
|---|---|---|---|
| | Mut 45_47 | Mut 104 | Mut 151_153 |
| Purity (%) | 92 | 96 | 89 |

The IAC result was a high degree of purity of hEPO muteins, which was considered suitable for use in the following tests. Thus, the IAC was established as an appropriate, simple and practical method for purification of hEPO muteins of the present invention.

5. Physicochemical Characterization of hEPO Muteins 5.1. Determination of Apparent Molecular Masses of the Different hEPO Muteins.

FIG. 9 shows a Western Blot of the muteins that were purified through immunoaffinity chromatography (IAC). It was used to calculate the molecular masses of such muteins using known molecular mass markers.

The determination of the apparent molecular masses of hEPO's hyperglycosylated muteins was carried out by interpolating the migration distances of the anterior and posterior front of the band corresponding to each variant in the variation curve of the distance migrated by each marker according to the log of its molecular mass. The apparent molecular masses calculated for each variant are summarized below:

Mut 45_47: 34-66 kDa
Mut 104: 29-66 kDa
Mut 151_153: 35-45 kDa
rhEPO: 31-43 kDa

This determination confirmed the success of the incorporation of an additional N-glycosylation site into the hEPO molecule, because muteins exhibited on average molecular masses greater than the molecular mass of the unmodified hEPO.

5.2. Determination of the Isoform Profile by IEF

In order to evaluate the degree of heterogeneity of hEPO muteins due to glycosylation and in particular, the content of sialic acid residues, samples were evaluated by IEF to determine the isoforms with different pI that make up each hEPO hyperglycosylated variant.

FIG. 10 shows the detection of 13 isoforms that make up the Mut 45_47 variant, 14 isoforms for the Mut 104 variant, and 6 isoforms for the standard rhEPO. It is worth mentioning that the rhEPO standard is the hormone produced as a biotherapeutic intended to favor erythropoiesis, in which there is a prevalence of the most acidic isoforms of the hEPO molecule, which are obtained after a purification process developed in 4 chromatographic steps. Additionally, it can be seen that muteins Mut 45_47 and Mut 104 contain 5-7 more acidic isoforms than rhEPO isoforms, reflecting a higher content of sialic acid in these molecules.

The data obtained in the determination of apparent molecular masses together with the data from the IEF confirm that the generated muteins have a higher degree of glycosylation when compared to rhEPO.

5.3. Analysis of the Isoform Profile by Means of Capillary Zone Electrophoresis (CZE) of IAC-Purified hEPO Muteins CZE was also used for the determination of isoforms for each hEPO variant that is considered as an application example. Processing was performed for samples obtained from IAC purifications of hEPO muteins diafiltered with water and concentrated to approximately 1 mg/ml.

CZE provides quantitative information on the different isoforms observed. Thus, using the CZE data, an isoform was assigned to each observed peak for each hEPO variant. For muteins Mut 45_47 and Mut 104 from 1 to 11, and for rhEPO standard from 1 to 7; isoform 1 was the isoform that migrated the most along the capillary zone (FIG. 11). Next, the percentages of each isoform were calculated by integrating the area under the curve of each peak.

When comparing the electrophoretic mobilities of the isoforms of each variant to rhEPO, it was found that the isoforms of the latter coincide with isoforms 1 to 7 of Mut 45_47 and with isoforms 3 to 9 of Mut 104, which shows that Mut 45_47 presents 4 more acidic isoforms when compared to rhEPO, while Mut 104 presents 2 less acidic isoforms and 2 more acidic isoforms when compared to rhEPO.

When evaluating the ratios of each isoform, it was shown that rhEPO has a higher ratio of isoforms 3, 4, and 5, while Mut 45_47 shows a higher ratio of isoforms 6, 7, 8, and 9, and Mut 104 shows a higher ratio of isoforms 4, 5, 6, and 7. This confirms once again the heterogeneity of each hEPO variant with respect to the degree of glycosylation of rhEPO due to the higher content of more acidic isoforms and their greater ratio.

When observing the electropherogram of each hEPO variant, the presence of two additional peaks (two more isoforms) can be visualized in both cases, one in front of peak 1 and another in front of peak 11, which could not be accurately resolved. This is due to the low ratio of such isoforms in the sample, which is lower than the detection limit of the system. This explains the difference in the number of isoforms detected by IEF and CZE.

5.4.a. Characterization of In Vitro Erythropoietic Biological Activity of Muteins The biological characterization of the purified and designed hEPO muteins was carried out. For this, in vitro proliferation assays were performed using UT-7 cell line cultures to evaluate the erythropoietic biological activity of the muteins that have been taken as application examples to show the embodiment of this invention (A-F), since the survival and proliferation of these cell lineages depend on the existence of hEPO in the growth medium. Unlike the assay that uses the TF-1 cell line, the assay that uses the UT-7 cell line is characterized by a higher sensitivity response, so it was selected for this stage of the work.

The culture supernatants of all muteins expressed from their respective production cell lines and the three IAC-purified muteins considered as examples, were analyzed. The proliferation developed by these molecules was compared to the proliferation developed by a rhEPO standard.

hEPO muteins that have been considered as application examples (except for Mut 49) exhibited low or no ability to stimulate cell proliferation when tested at the same concentrations as the rhEPO standard (FIG. 12-a-). In order to calculate a specific erythropoietic activity (SEA) evaluated in vitro, we worked with higher concentrations of the muteins, that is, those present in pure culture supernatants. Thus, muteins Mut 104 and Mut 151_153 showed complete loss of erythropoietic biological activity, while Mut 45_47, Mut 62_64, and Mut 98_100 showed very low erythropoietic activity (SEAmut 45_47=0.2 UI/µg, SEAmut 62_64=0.2 UI/µg, and SEAmut 98_100=0.1 UI/µg, when compared to SEA=120 UI/µg for rhEPO). On the contrary, it was considered that Mut 49 maintained such activity (SEA=216 UI/µg). Although there was an increase in Mut 49 SEA, this may be due to the zone of the curve that was used to determine such parameter, given that the slope of the linear response zone of Mut 49 curve was markedly different from the one of the standard. Thus, the modification made to obtain such mutein was not considered efficient to inhibit its erythropoietic activity.

Additionally, the in vitro cyto/neuroprotective biological activity of the purified rhEPO muteins was analyzed as an application example of the present invention. An evaluation was performed to study the cyto/neuroprotective activity, the ability of rhEPO and its muteins to protect SH-SY5Y neuronal cells from the apoptotic/cytotoxic effect generated by staurosporine (STP). Thus, the cyto/neuroprotection assay consisted of protecting neuronal cells by adding rhEPO or its muteins 12 h prior to induction of cellular damage caused by STP. After cell damage induction time, the viability of the cultures was evaluated by determining metabolically active cells.

In this assay, both rhEPO and purified Mut 104—considered as an application example of the invention—were used at the same concentrations (FIG. 13).

The results obtained were statistically analyzed using the ANOVA test, followed by the Dunnet test, in order to compare each of the samples with CSTP. The cytotoxicity percentage obtained for CSTP was considered as 100% cytotoxicity, and consequently, the cytotoxicity values determined for each of the samples were calculated in relation to CSTP.

As it is shown in FIG. 13, rhEPO was able to reduce the cytotoxicity induced by STP by 45% ($p<0.05$), while Mut 104 showed a significant decrease in cytotoxicity caused by STP, reducing it by 65% with a degree of significance of 99% ($p<0.01$).

5.4.b. Characterization of In Vivo Erythropoietic Biological Activity of Muteins.

The muteins used as an application example have no or little in vitro biological activity. In turn, extensive glycosylation confers pharmacokinetic properties necessary to increase the residence time in blood. These characteristics would allow the molecules to improve the low capacity for interaction with the receptor and to demonstrate erythropoietic activity.

To evaluate such in vivo activity, normocytemic mice were injected with rhEPO as standard or with each of the three muteins used in the previous examples, or with PBS as negative control. In all cases corresponding to protein inoculation, a protein mass equivalent to 80 IU of rhEPO was used. Blood was collected 96 h after inoculation, and flow cytometry was used to determine the percentage content of thiazole orange-labeled reticulocytes.

FIG. 12-b-shows a significantly different response ($p<0.001$) of each mutein and the negative control with respect to rhEPO. Additionally, no significant differences were observed when comparing the reticulocytes response generated by each mutein with the negative control. Both types of analysis confirm the expected loss of erythropoietic activity of the muteins as a result of the N-glycoengineering by hyperglycosylation approach.

5.5. Effect of hEPO Hyperglycosylated Muteins in the Structural Neuronal Plasticity 5.5.1. Neuronal Development (Differentiation) and Structural Plasticity Structural neuronal plasticity encompasses the processes by which neuronal development and/or differentiation are stimulated or favored. In this sense, chemical agents or compounds that promote the formation of neurites and/or axonal growth, the development of filopodia/dendritic spines and/or increase the number of synapses will be considered as neurotrophic compounds. Primary cultures of neurons and neuronal cell lines have been widely used for the in vitro study of such processes.

The stages of neuronal development in primary cultures of hippocampal neurons are outlined in FIG. 14. These stages have been properly characterized in the work of Dotti et al. (1998) [31] where it is described that, after being seeded, neurons develop lamellae with which they adhere to the substrate (0 DIV, days of in vitro culture). Then, during the first two days (1-2 DIV) immature neurites develop as extensions of the plasma membrane. At 2-3 DIV one of these neurites stretches beyond the rest and differentiates to form the axon, which has at its end a triangular structure known as axonal growth cone. Afterwards, neurites branch off forming the secondary neurites (3-4 DIV). Thin cytoplasmic projections are developed over these neurites that contain cross-linked actin filaments known as filopodia (4-5 DIV). Filopodia can then lead to dendritic spines that are the preferential sites where synapses occur (7-21 DIV).

This part of the study evaluated the neurotrophic action of different hEPO hyperglycosylated muteins of the invention at different stages of neuronal development.

5.5.2. Formation of Neurites

To determine if the muteins of the present invention produced a neuritogenic effect (increase in the number and length of neurites per neuron), the N2a neuronal cell line (mice neuroblastoma) was used. Cells (50,000) were seeded on glasses in culture plates (24 wells) and maintained in DMEM complete medium, supplemented with 20% (V/V) of fetal bovine serum (FBS) that inhibits neuronal differentiation, and gentamicin as an antibiotic. Then, the culture medium was replaced by a medium without FBS supplemented with different concentrations (50 and 300 ng/ml) of rhEPO, or the muteins for 3 hrs to induce neuritogenesis [32]. After that time, cells were fixed with paraformaldehyde 4% (PFA) with sucrose 4% in phosphate-buffered saline (PBS) at 4° C. for 10 minutes and permeabilized with 0.1% (V/V) Triton X-100 in PBS for 2 minutes. Fixed cells were then blocked with 3% (W/V) of bovine serum albumin (BSA) in PBS for 1-2 h with mouse anti-alpha-tubulin IgG monoclonal antibody in 1% (W/V) BSA (1:1000, Sigma) to mark neurites for 16 h at 4° C. The next day, after 3 washings with PBS, it was incubated with rhodamine-conjugated phalloidin to label actin filaments (1:1000, Invitrogen) and with goat anti-mouse antibodies conjugated to Alexa 488 (1:1000, Invitrogen) for 1 h at room temperature. After three washings with cold PBS for 5 minutes, the glasses were mounted with Fluorsave (Calbiochem).

To quantify neuritogenesis, images were acquired with a Nikon TE2000 epifluorescence microscope (Nikon). Quantification was performed by counting the number of neurites and their average length (extension of neurites) and the length of the longest neurite (axonal growth) in at least 30 neurons per condition using Image J (NIH) software's NeuroJ plug-in. Representative images were then processed with Adobe Photoshop, and statistical analysis was performed with the software GraphPadPrism 5.

FIG. 15-a-shows representative images of each of the groups studied. The statistical analysis of each of the measurements is detailed on the right. The muteins of the present invention have a significant dose-dependent neurogenic effect that is manifested by an increase in the number of neurites per neuron, the extension of neurites and axonal growth. These effects are comparable, giving similar values to those obtained for rhEPO. In other words, the muteins of the present invention showed a neurotrophic effect similar to that observed for rhEPO in the N2a cell line.

5.5.3. Filopodia Density

Filopodia and dendritic spines are membrane protrusions enriched with actin filaments which emerge from the neurite/dendrite and act as post-synaptic compartments that are very abundant in excitatorial synapses of the central nervous system. The morphology of the spines is variable and they are classified according to their differential structure. It is accepted that dendritic spines can change their shape/structure during neuronal development favoring neuronal plasticity [33]. In this sense, certain neurodegenerative diseases have been related to changes in the shape and number of dendritic spines (both increase and decrease). In Down syndrome, for example, it was determined that the amount of spines is severely reduced [34]. In contrast, spines are found in higher amounts in autism spectrum disorders [35].

Therefore, the ability to induce neuronal plasticity was determined by promoting the formation of filopodia of the hyperglycosylated muteins of the present invention. We used primary cultures of hippocampal neurons exposed to different concentrations (50 and 300 ng/ml) of rhEPO, or of muteins Mut 104, Mut 45-47, and Mut 151-153 for 4 days (4 DIV).

Neuronal cultures were prepared from rat embryos hippocampus (E19) as it was previously described [36]. Briefly, the tissue was treated with trypsin-EDTA (0.25% (W/V)) at 37° C. for 15 minutes. A solution of completely dispersed cells was prepared in Neurobasal Medium (NB, Invitrogen) supplemented with 2 mM glutamine, 100 units/ml penicillin (PEN), 100 µg/ml streptomycin (Strp), and 10% (V/V) horse serum. A number of 20,000-30,000 cells were seeded in 24-well culture plates previously treated with 0.1 mg/ml poly-L-lysine hydrobromide (Sigma) and 20 mg/ml laminin (Invitrogen). After 2 h, the medium was changed to a defined medium (NB with 1 g/l ovalbumin; N2 and B27 which are serum-free supplements from Invitrogen) and added with different concentrations (50 and 300 ng/ml) rhEPO, or muteins of the present invention and maintained for 4 DIV. Cells were fixed with 4% (W/V) PFA 4% (W/V) sucrose in PBS at 4° C. for 10 minutes. Then, cells were permeabilized with 0.1% (V/V) Triton X-100 in PBS for 2 minutes. Fixed cells were then blocked with 3% (W/V) of bovine serum albumin (BSA) in PBS for 1-2 h and incubated for h at 4° C. with mouse anti-alpha-tubulin IgG monoclonal antibody in 1% (W/V) BSA (1:1000, Sigma) to mark neurites. The next day, after three washings with PBS, it was incubated with rhodamine-conjugated phalloidin to label actin filaments (1:1000, Invitrogen) and with the secondary goat anti-mouse antibody conjugated to Alexa 488 (1:1000, Invitrogen) for 1 h at room temperature. After three washings with cold PBS for 5 minutes, the glasses were mounted with Fluorsave (Calbiochem).

To quantify filopodia formation, images were acquired with a Nikon E600 epifluorescence microscope (Nikon). The quantification was performed by counting the number of filopodia (actin-rich protrusions protruding from the neurite membrane) present in 20 µm of neurite at a distance less than 50 µm from the neuronal soma (3 neurites/neuron in at least 30 neurons). Representative images were then processed with Adobe Photoshop, and statistical analysis was performed with the software GraphPadPrism 5.

FIG. 16 (panel on the left) shows representative images of the density of filopodia, while the panel on the right details the statistical analysis for each of the groups. It is noted that the muteins of the present invention significantly induce, depending on the dose, the filopodia formation when compared with control neurons (PBS). Surprisingly, these effects are still superior to those observed for neurons treated with rhEPO. In summary, the muteins of the present invention showed a neurotrophic effect in primary cultures of hippocampal neurons that was superior to that observed for rhEPO.

5.5.3. Synapses

Synapse is defined as the specialized contiguity relations (union) of membranes between two neurons. This union (known as the synaptic cleft) facilitates the conduction of the electrical impulse and the passage of substances from one of them (pre-synaptic) and the other (post-synaptic). Different techniques have been developed to quantify the number of synapses. Thus, an accepted definition of synapse is the co-occurrence of protein clusters exclusively from a pre-synaptic compartment with protein clusters exclusively from a post-synaptic compartment.

Continuing with the study of the neurotrophic effect of the muteins of the present invention, their ability to induce neuronal synapses was evaluated.

For this, an immunodetection assay was performed in a 15 DIV primary neuronal culture in which synapse formation is detected by overlapping a pre- and a post-synaptic marker.

Shortly, neurons (15,000/well) were treated with different concentrations (50 and 300 ng/ml) of hEPO muteins, or with rhEPO, or with PBS for 15 DIV. Then they were fixed with a solution of 90% (V/V) methanol and 10% (V/V) MES (100 mM MES pH 6.9, 1 mM EGTA, 1 mM MgCl2) at 4° C. for 10 minutes. Afterwards, they were washed three times with PBS filtered with Tween 20 (0.1% (V/V)) for 5 minutes. Blocking was performed with a solution of FBS with Triton X-100 (10% FBS (V/V), Triton X-100 0.1% (V/V) in PBS) for 1 h at room temperature, and then they were incubated with a solution of 3% (W/V) BSA also in PBS for 15 minutes at room temperature. Both blocking solutions were previously centrifuged for 10 minutes at maximum speed. Then, they were incubated 12-16 h at 4° C. with the primary mouse anti-NMDA-R1 antibody (post-synaptic marker from Synaptic Systems) and the rabbit anti-synaptophysin antibody (pre-synaptic marker from Synaptic Systems). Both antibodies were prepared in a 1% (W/V) PBS-BSA solution, and centrifuged for 10 minutes at maximum speed. After washing three times with PBS, they were blocked again with 3% (W/V) BSA centrifuged for 10 minutes and with the 10% (V/V) FBS solution, Triton X-100 0.1% (V/V) PBS for 1 h at room temperature. They were then incubated with the secondary anti-mouse antibodies conjugated to Alexa 647 and anti-rabbit antibodies conjugated to Alexa 568 prepared in 1% (W/V) BSA and centrifuged 10 minutes at maximum speed (both from Molecular Probes). Then they were mounted with Fluorsave.

The photos were taken with an Olympus FV1000 confocal microscope associated with an Olympus IX81 inverted microscope. The images were processed sequentially with the software FluoView (version 3.3, Olympus; 60× objective; AN 1.42; 0.066 µm/pixel resolution), compliant with Nyquist criteria.

Synapse formation was measured as co-localization points in 25 µm dendrite between the pre-synaptic marker and the post-synaptic marker, in approximately 10 to 20 neurons per condition using 3 segments per neuron. These co-localization points were determined using the Puncta analyzer, an Image J plug-in (version 1.28u) [37].

FIG. 17 shows a representative photo of each of the conditions tested and their corresponding quantification. As in the case of neuritogenesis and filopodia induction, we observed that muteins significantly induce the formation of new synapses in neuronal culture. This effect is similar to that observed for rhEPO.

Considering the abovementioned data, there is strong experimental evidence that shows that the new hyperglycosylated hEPO muteins of the present invention have a neuronal plasticity facilitating effect at different stages of neuronal development/differentiation (from the formation of neurites to synapse formation). Moreover, these effects are comparable to those observed for EPO and, in some particular cases the effects (filopodia formation) are even greater. These surprising and novel technical effects and the innovative technical characteristics of the present invention make the muteins of the present invention ideal for use in treatments where neuronal plasticity is diminished or there is a genetic predisposition to such decrease.

5.6.b. Study of the Neuroprotective Biological Activity of rhEPO Muteins in Primary Cultures of Rat Hippocampal Neurons.

The evaluation of hEPO muteins antiapoptotic effect on primary cultures of hippocampal neurons allows us to study the effect that these compounds have in cells whose metabolism is not altered as in the established cell lines. For this reason, it constitutes an interesting model as it is more realistically similar to what would happen in vivo in the brain.

The neuroprotective activity of hEPO and the modified erythropoietins of the present invention was evaluated as the ability of such molecules to protect neuronal cells from apoptotic stimulation induced by treatment with staurosporine.

To evaluate such in vitro activity, primary cultures of hippocampal neurons from Sprague-Dawley rats were obtained. 11 DIV cultures were pretreated for 24 h with 400 ng/ml of hEPO muteins from the present invention or with 400 ng/ml of the rhEPO usually used for the treatment of hematopoiesis recovery. After this time, cells were exposed to 30 nM STP for 24 h in the presence of the molecules and, finally, they were fixed and colored with Hoechst fluorochrome and with Phalloidin-FITC.

FIG. 18 shows that the treatment with the different molecules significantly reduced apoptosis ($p<0.01$; *$p<0.001$) when compared to cell death control (cells treated only with STP), reaching apoptosis values similar to the cell control without STP. Additionally, most of the molecules of this invention showed an effect that was superior to that of rhEPO in terms of protecting primary cultures of hippocampal neurons from the effect of STP.

The results also correspond to those obtained in the study of neuroprotective activity of the muteins on SH-SY5Y neuronal cultures. Therefore, the addition of an extra glycosylation site to obtain the molecules of the present invention allowed blocking its hematopoietic biological activity without modifying the one related to neuroprotection.

BIBLIOGRAPHY

[1] J. W. Fisher. Exp Biol Med (Maywood) 228 (2003) 1-14.
[2] C. Lacombe, P. Mayeux. Nephrol Dial Transplant 14 Suppl 2 (1999) 22-28.
[3] U. Hammerling, R. Kroon, T. Wilhelmsen, L. Sjodin, J. Pharm Biomed Anal 14 (1996) 1455-1469.
[4] H. Sasaki, B. Bothner, A. Dell, M. Fukuda. J Biol Chem 262 (1987) 12059-12076.
[5] E. Tsuda, M. Goto, A. Murakami, K. Akai, M. Ueda, G. Kawanishi, N. Takahashi, R. Sasaki, H. Chiba, H. Ishihara, et al. Biochemistry 27 (1988) 5646-5654.
[6] J. C. Egrie, J. K. Browne. Br J Cancer 84 Suppl 1 (2001) 3-10.
[7] A. J. Sytkowski, L. Feldman, D. J. Zurbuch, Biochem Biophys Res Commun 176 (1991) 698-704.
[8] E. Delorme, T. Lorenzini, J. Giffin, F. Martin, F. Jacobsen, T. Boone, S. Elliott. Biochemistry 31 (1992) 9871-9876.
[9] T. Toyoda, T. Arakawa, H. Yamaguchi. J Biochem 131 (2002) 511-515.
[10] Nangaku, M. Kidney International (2013) 84, 427-429.
[11] T Ng, G Marx, T Littlewood, I Macdougall. Postgrad Med J (2003) 79: 367-376
[12] N. Debeljak, A. J. Sytkowski, Erythropoietin: new approaches to improved molecular designs and therapeutic alternatives. Curr Pharm Des 14 (2008) 1302-1310.
[13] Noguchi, C. T., Asavaritikrai, P., Teng, R., and Jia, Y. (2007). Role of erythropoietin in the brain. Crit Rev Oncol Hematol 64, 159-171.
[14] P. a. Konstantinopoulos, M. V. Karamouzis, A. G. Papavassiliou. Biochim. Biophys. Acta 1776 (2007) 1-9.
[15] Siren, A. L. y Ehrenreich, H. Eur. Arch. Psychiatry Clin. Neurosci. (2001) 251(4): 179-184.
[16] Neurodegenerative disorders, Public health—European commission. http://ec.europa.eu/health/major chronic diseases/diseases/brain neurological/index en.htm
[17] Policy Brief: The Global Impact of Dementia 2013-2050—The Global voice on Dementia. Alzheimer's disease International. http://www.alz.co.uk/research/G8-policy-brief.
[18] NIH meeting advances Alzheimer's research agenda. Fogarty International Center. Advancing Science for Global Health. http://www.fic.nih.gov/news/globalhealth-matters/march-april-2015/pages/nih-alzheimers-research-summit.aspx
[19] Toledo Atucha, J. Alzheimer. Real Invest Demenc. (2011), 47: 16-23.
[20] Mawadda Alnaeeli, LiWang, Barbora Piknova, Heather Rogers, Xiaoxia Li, and Constance Tom Noguchi. Anatomy Research International. Volume 2012, Article ID 953264, 15 pages
[21] Masuda, S. y col. J. Biol. Chem. (1993) 268(15): 11208-11216.
[22] Wolf y col. Thromb Haemost (1997), 77:1020 1024.
[23] P. J. Stohlawetz, L. Dzirlo, N. Hergovich, E. Lackner, C. Mensik, H. G. Eichler, E. Kabrna, K. Geissler, B. Jilma. Blood 95 (2000) 2983-2989.
[24] Cases A y col. Kidney Internacional (1992), 42:668-672.
[25] Beguin Y., Haematologica (1999), 84:541-547.
[26] M. Leist, P. Ghezzi, G. Grasso, R. Bianchi, P. Villa, M. Fratelli, C. Savino, M. Bianchi, J. Nielsen, J. Gerwien, P. Kallunki, A. K. Larsen, L. Helboe, S. Christensen, L. O. Pedersen, M. Nielsen, L. Torup, T. Sager, A. Sfacteria, S. Erbayraktar, Z. Erbayraktar, N. Gokmen, O. Yilmaz, C. Cerami-Hand, Q. W. Xie, T. Coleman, A. Cerami, M. Brines. Science 305 (2004) 239-242.
[27] T. Mennini, M. De Paola, P. Bigini, C. Mastrotto, E. Fumagalli, S. Barbera, M. Mengozzi, B. Viviani, E. Corsini, M. Marinovich, L. Torup, J. Van Beek, M. Leist, M. Brines, A. Cerami, P. Ghezzi. Mol. Med. 12 (2006) 153-160.
[28] Siren, A. L. y col. Neurotherapeutics (2009), 6(1): 108-127.
[29] Erbayraktar, S. y col. Proc. Natl. Acad. Sci. (2003), USA 100: 6741-6746.
[30] M. Mattio, N. Ceaglio, M. Oggero, N. Perotti, I. Amadeo, G. Orozco, G. Forno, R. Kratje, M. Etcheverrigaray. Biotechnol Prog 27 (2011) 1018-1028.
[31] Dotti C G, Sullivan C A, Banker G A. 1988. J Neurosci (1988) 8:1454-1468
[32] Das K P, Freudenrich T M, Mundy W R. Neurotoxicol Teratol (2004) 26:397-406
[33] Rochefort N L, Konnerth A. EMBO Rep. (2012) August; 13(8):699-708. DOI: 10.1038/embor.2012.102.
[34] Suetsugu M, Mehraein P. Acta Neuropathol. (1980)50 (3):207-10.
[35] Hutsler J J1, Zhang H. Brain Res. (2010) January 14; 1309:83-94. DOI: 10.1016/j.brainres.2009.09.120.
[36] Alfonso J., Fernandez M. E., Cooper B., Flugge G. and Frasch A. C. Proc. Natl Acad. Sci. (2005) USA 102, 17196-17201.
[37] Ippolito, D. M., Eroglu, C., Journal of Visualized Experiments. (2010) Exp. 45:2270. DOI: 10.3791/2270.

The invention claimed is:

1. A modified mature human erythropoietin with erythropoietic activity less than 0.5% in relation to a native erythropoietin, which maintains its neuroprotective and neuroplastic capacity, comprising mutations of a binding site to a homodimeric or heterodimeric receptor through the addition of consensus sites for glycosylation, the mutations comprising:

Lys45Asn and Asn47Thr, wherein said modified mature human erythropoietin comprises SEQ ID NO: 4.

2. The modified human erythropoietin of claim 1, comprising no erythropoietic activity.

3. A pharmaceutical composition comprising a therapeutically effective amount of the modified human erythropoietin of claim 1.

* * * * *

SEQUENCE LISTING

```
<160> NUMBER OF SEQ ID NOS: 26

<210> SEQ ID NO 1
<211> LENGTH: 495
<212> TYPE: DNA
<213> ORGANISM: Artificial Sequence
<220> FEATURE:
<223> OTHER INFORMATION: DNA MUTEIN 15_17

<400> SEQUENCE: 1
gctcctccta gactgatctg cgactcccgg gtgctggaaa gaaacctgac ggaagccaaa    60
```

```
gaggccgaga acatcaccac cggctgcgcc gagcactgct ccctgaacga gaatatcacc    120
gtgcccgaca ccaaagtgaa cttctacgcc tggaagcgga tggaagtggg ccagcaggct    180
gtggaagtgt ggcagggact ggctctgctg agcgaggctg tgctgagagg acaggccctg    240
ctcgtgaact cctcccagcc ttgggaaccc ctgcagctgc acgtggacaa ggctgtgtcc    300
ggcctgagat ccctgaccac cctgctgaga gcactgggag cccagaaaga ggccatctct    360
ccacctgacg ccgcctctgc tgctcctctg agaaccatca ccgccgacac cttcagaaag    420
ctgttccggg tgtactccaa cttcctgcgg ggcaagctga agctgtacac cggcgaggct    480
tgccggaccg gcgac                                                     495

<210> SEQ ID NO 2
<211> LENGTH: 165
<212> TYPE: PRT
<213> ORGANISM: Artificial Sequence
<220> FEATURE:
<223> OTHER INFORMATION: AA - MUTEIN 15_17

<400> SEQUENCE: 2

Ala Pro Pro Arg Leu Ile Cys Asp Ser Arg Val Leu Glu Arg Asn Leu
1               5                  10                  15

Thr Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 3
<211> LENGTH: 495
<212> TYPE: DNA
<213> ORGANISM: Artificial Sequence
<220> FEATURE:
<223> OTHER INFORMATION: DNA MUTEIN 45_47

<400> SEQUENCE: 3
gctcctccta gactgatctg cgactcccgg gtgctggaaa gatacctgct ggaagccaaa     60
gaggccgaga acatcaccac cggctgcgcc gagcactgct ccctgaacga gaatatcacc    120
gtgcccgaca ccaacgtgac cttctacgcc tggaagcgga tggaagtggg ccagcaggct    180
gtggaagtgt ggcagggact ggctctgctg agcgaggctg tgctgagagg acaggccctg    240
ctcgtgaact cctcccagcc ttgggaaccc ctgcagctgc acgtggacaa ggctgtgtcc    300
```

```
ggcctgagat ccctgaccac cctgctgaga gcactgggag cccagaaaga ggccatctct    360
ccacctgacg ccgcctctgc tgctcctctg agaaccatca ccgccgacac cttcagaaag    420
ctgttccggg tgtactccaa cttcctgcgg ggcaagctga agctgtacac cggcgaggct    480
tgccggaccg gcgac                                                     495

<210> SEQ ID NO 4
<211> LENGTH: 165
<212> TYPE: PRT
<213> ORGANISM: Artificial Sequence
<220> FEATURE:
<223> OTHER INFORMATION: AA - MUTEIN 45_47

<400> SEQUENCE: 4

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Asn Val Thr Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 5
<211> LENGTH: 495
<212> TYPE: DNA
<213> ORGANISM: Artificial Sequence
<220> FEATURE:
<223> OTHER INFORMATION: DNA MUTEIN 49

<400> SEQUENCE: 5
gctcctccta gactgatctg cgactcccgg gtgctggaaa gatacctgct ggaagccaaa     60
gaggccgaga acatcaccac cggctgcgcc gagcactgct ccctgaacga gaatatcacc    120
gtgcccgaca ccaaagtgaa cttcaccgcc tggaagcgga tggaagtggg ccagcaggct    180
gtggaagtgt ggcagggact ggctctgctg agcgaggctg tgctgagagg acaggccctg    240
ctcgtgaact cctcccagcc ttgggaaccc ctgcagctgc acgtggacaa ggctgtgtcc    300
ggcctgagat ccctgaccac cctgctgaga gcactgggag cccagaaaga ggccatctct    360
ccacctgacg ccgcctctgc tgctcctctg agaaccatca ccgccgacac cttcagaaag    420
ctgttccggg tgtactccaa cttcctgcgg ggcaagctga agctgtacac cggcgaggct    480
tgccggaccg gcgac                                                     495
```

<210> SEQ ID NO 6
<211> LENGTH: 165
<212> TYPE: PRT
<213> ORGANISM: Artificial Sequence
<220> FEATURE:
<223> OTHER INFORMATION: AA - MUTEIN 49

<400> SEQUENCE: 6

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Thr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```

<210> SEQ ID NO 7
<211> LENGTH: 495
<212> TYPE: DNA
<213> ORGANISM: Artificial Sequence
<220> FEATURE:
<223> OTHER INFORMATION: DNA - MUTEIN 62_64

<400> SEQUENCE: 7

```
gctcctccta gactgatctg cgactcccgg gtgctggaaa gatacctgct ggaagccaaa      60
gaggccgaga acatcaccac cggctgcgcc gagcactgct ccctgaacga gaatatcacc     120
gtgcccgaca ccaaagtgaa cttctacgcc tggaagcgga tggaagtggg ccagcaggct     180
gtgaacgtga cgcagggact ggctctgctg agcgaggctg tgctgagagg acaggccctg     240
ctcgtgaact cctcccagcc ttgggaaccc ctgcagctgc acgtggacaa ggctgtgtcc     300
ggcctgagat ccctgaccac cctgctgaga gcactgggag cccagaaaga ggccatctct     360
ccacctgacg ccgcctctgc tgctcctctg agaaccatca ccgccgacac cttcagaaag     420
ctgttccggg tgtactccaa cttcctgcgg ggcaagctga agctgtacac cggcgaggct     480
tgccggaccg gcgac                                                      495
```

<210> SEQ ID NO 8
<211> LENGTH: 165
<212> TYPE: PRT
<213> ORGANISM: Artificial Sequence
<220> FEATURE:
<223> OTHER INFORMATION: AA - MUTEIN 62_64

<400> SEQUENCE: 8

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Asn Val Thr
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 9
<211> LENGTH: 495
<212> TYPE: DNA
<213> ORGANISM: Artificial Sequence
<220> FEATURE:
<223> OTHER INFORMATION: DNA - MUTEIN 65_67

<400> SEQUENCE: 9
gctcctccta gactgatctg cgactcccgg gtgctggaaa gatacctgct ggaagccaaa      60
gaggccgaga acatcaccac cggctgcgcc gagcactgct ccctgaacga gaatatcacc     120
gtgcccgaca ccaaagtgaa cttctacgcc tggaagcgga tggaagtggg ccagcaggct     180
gtggaagtgt ggaacggaac ggctctgctg agcgaggctg tgctgagagg acaggccctg     240
ctcgtgaact cctcccagcc ttgggaaccc ctgcagctgc acgtggacaa ggctgtgtcc     300
ggcctgagat ccctgaccac cctgctgaga gcactgggag cccagaaaga ggccatctct     360
ccacctgacg ccgcctctgc tgctcctctg agaaccatca ccgccgacac cttcagaaag     420
ctgttccggg tgtactccaa cttcctgcgg ggcaagctga agctgtacac cggcgaggct     480
tgccggaccg gcgac                                                     495

<210> SEQ ID NO 10
<211> LENGTH: 165
<212> TYPE: PRT
<213> ORGANISM: Artificial Sequence
<220> FEATURE:
<223> OTHER INFORMATION: AA - MUTEIN 65_67

<400> SEQUENCE: 10

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Asn Gly Thr Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 11
<211> LENGTH: 495
<212> TYPE: DNA
<213> ORGANISM: Artificial Sequence
<220> FEATURE:
<223> OTHER INFORMATION: DNA - MUTEIN 72_74

<400> SEQUENCE: 11
gctcctccta gactgatctg cgactcccgg gtgctggaaa gatacctgct ggaagccaaa      60
gaggccgaga acatcaccac cggctgcgcc gagcactgct ccctgaacga gaatatcacc     120
gtgcccgaca ccaaagtgaa cttctacgcc tggaagcgga tggaagtggg ccagcaggct     180
gtggaagtgt ggcagggact ggctctgctg agcaacgcta cgctgagagg acaggccctg     240
ctcgtgaact cctcccagcc ttgggaaccc ctgcagctgc acgtggacaa ggctgtgtcc     300
ggcctgagat ccctgaccac cctgctgaga gcactgggag cccagaaaga ggccatctct     360
ccacctgacg ccgcctctgc tgctcctctg agaaccatca ccgccgacac cttcagaaag     420
ctgttccggg tgtactccaa cttcctgcgg ggcaagctga agctgtacac cggcgaggct     480
tgccggaccg gcgac                                                      495

<210> SEQ ID NO 12
<211> LENGTH: 165
<212> TYPE: PRT
<213> ORGANISM: Artificial Sequence
<220> FEATURE:
<223> OTHER INFORMATION: AA - MUTEIN 72_74

<400> SEQUENCE: 12

Ala Pro Pro Arg Leu Ile Cys Asp Ser Arg Val Leu Glu Arg Tyr Leu
 1                5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Asn Ala Thr Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
            165

<210> SEQ ID NO 13
<211> LENGTH: 495
<212> TYPE: DNA
<213> ORGANISM: Artificial Sequence
<220> FEATURE:
<223> OTHER INFORMATION: DNA - MUTEIN 76_78

<400> SEQUENCE: 13
gctcctccta gactgatctg cgactcccgg gtgctggaaa gatacctgct ggaagccaaa      60
gaggccgaga acatcaccac cggctgcgcc gagcactgct ccctgaacga gaatatcacc     120
gtgcccgaca ccaaagtgaa cttctacgcc tggaagcgga tggaagtggg ccagcaggct     180
gtggaagtgt ggcagggact ggctctgctg agcgaggctg tgctgaacgg aacggccctg     240
ctcgtgaact cctcccagcc ttgggaaccc ctgcagctgc acgtggacaa ggctgtgtcc     300
ggcctgagat ccctgaccac cctgctgaga gcactgggag cccagaaaga ggccatctct     360
ccacctgacg ccgcctctgc tgctcctctg agaaccatca ccgccgacac cttcagaaag     420
ctgttccggg tgtactccaa cttcctgcgg ggcaagctga agctgtacac cggcgaggct     480
tgccggaccg gcgac                                                     495

<210> SEQ ID NO 14
<211> LENGTH: 165
<212> TYPE: PRT
<213> ORGANISM: Artificial Sequence
<220> FEATURE:
<223> OTHER INFORMATION: AA - MUTEIN 76_78

<400> SEQUENCE: 14

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Asn Gly Thr Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala

```
                115                 120                 125
Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 15
<211> LENGTH: 495
<212> TYPE: DNA
<213> ORGANISM: Artificial Sequence
<220> FEATURE:
<223> OTHER INFORMATION: DNA - MUTEIN 98_100

<400> SEQUENCE: 15
gctcctccta gactgatctg cgactcccgg gtgctggaaa gatacctgct ggaagccaaa    60
gaggccgaga acatcaccac cggctgcgcc gagcactgct ccctgaacga gaatatcacc   120
gtgcccgaca ccaaagtgaa cttctacgcc tggaagcgga tggaagtggg ccagcaggct   180
gtggaagtgt ggcagggact ggctctgctg agcgaggctg tgctgagagg acaggccctg   240
ctcgtgaact cctcccagcc ttgggaaccc ctgcagctgc acgtggacaa gaatgtgacc   300
ggcctgagat ccctgaccac cctgctgaga gcactgggag cccagaaaga ggccatctct   360
ccacctgacg ccgcctctgc tgctcctctg agaaccatca ccgccgacac cttcagaaag   420
ctgttccggg tgtactccaa cttcctgcgg ggcaagctga agctgtacac cggcgaggct   480
tgccggaccg gcgac                                                    495

<210> SEQ ID NO 16
<211> LENGTH: 165
<212> TYPE: PRT
<213> ORGANISM: Artificial Sequence
<220> FEATURE:
<223> OTHER INFORMATION: AA - MUTEIN 98_100

<400> SEQUENCE: 16

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Asn Val Thr Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160
```

Cys Arg Thr Gly Asp
            165

<210> SEQ ID NO 17
<211> LENGTH: 495
<212> TYPE: DNA
<213> ORGANISM: Artificial Sequence
<220> FEATURE:
<223> OTHER INFORMATION: DNA - MUTEIN 104

<400> SEQUENCE: 17

| | |
|---|---:|
| gctcctccta gactgatctg cgactcccgg gtgctggaaa gatacctgct ggaagccaaa | 60 |
| gaggccgaga acatcaccac cggctgcgcc gagcactgct ccctgaacga gaatatcacc | 120 |
| gtgcccgaca ccaaagtgaa cttctacgcc tggaagcgga tggaagtggg ccagcaggct | 180 |
| gtggaagtgt ggcagggact ggctctgctg agcgaggctg tgctgagagg acaggccctg | 240 |
| ctcgtgaact cctcccagcc ttgggaaccc ctgcagctgc acgtggacaa ggctgtgtcc | 300 |
| ggcctgagaa acctgaccac cctgctgaga gcactgggag cccagaaaga ggccatctct | 360 |
| ccacctgacg ccgcctctgc tgctcctctg agaaccatca ccgccgacac cttcagaaag | 420 |
| ctgttccggg tgtactccaa cttcctgcgg ggcaagctga agctgtacac cggcgaggct | 480 |
| tgccggaccg gcgac | 495 |

<210> SEQ ID NO 18
<211> LENGTH: 165
<212> TYPE: PRT
<213> ORGANISM: Artificial Sequence
<220> FEATURE:
<223> OTHER INFORMATION: AA - MUTEIN 104

<400> SEQUENCE: 18

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Asn Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
            165

<210> SEQ ID NO 19
<211> LENGTH: 495
<212> TYPE: DNA
<213> ORGANISM: Artificial Sequence

<220> FEATURE:
<223> OTHER INFORMATION: DNA - MUTEIN 106_108

<400> SEQUENCE: 19

```
gctcctccta gactgatctg cgactcccgg gtgctggaaa gatacctgct ggaagccaaa      60
gaggccgaga acatcaccac cggctgcgcc gagcactgct ccctgaacga gaatatcacc     120
gtgcccgaca ccaaagtgaa cttctacgcc tggaagcgga tggaagtggg ccagcaggct     180
gtggaagtgt ggcagggact ggctctgctg agcgaggctg tgctgagagg acaggccctg     240
ctcgtgaact cctcccagcc ttgggaaccc ctgcagctgc acgtggacaa ggctgtgtcc     300
ggcctgagat ccctgaacac cacgctgaga gcactgggag cccagaaaga ggccatctct     360
ccacctgacg ccgcctctgc tgctcctctg agaaccatca ccgccgacac cttcagaaag     420
ctgttccggg tgtactccaa cttcctgcgg ggcaagctga agctgtacac cggcgaggct     480
tgccggaccg gcgac                                                      495
```

<210> SEQ ID NO 20
<211> LENGTH: 165
<212> TYPE: PRT
<213> ORGANISM: Artificial Sequence
<220> FEATURE:
<223> OTHER INFORMATION: AA - MUTEIN 106_108

<400> SEQUENCE: 20

```
Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Asn Thr Thr Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
            165
```

<210> SEQ ID NO 21
<211> LENGTH: 495
<212> TYPE: DNA
<213> ORGANISM: Artificial Sequence
<220> FEATURE:
<223> OTHER INFORMATION: DNA - MUTEIN 149

<400> SEQUENCE: 21

```
gctcctccta gactgatctg cgactcccgg gtgctggaaa gatacctgct ggaagccaaa      60
gaggccgaga acatcaccac cggctgcgcc gagcactgct ccctgaacga gaatatcacc     120
```

```
gtgcccgaca ccaaagtgaa cttctacgcc tggaagcgga tggaagtggg ccagcaggct    180
gtggaagtgt ggcagggact ggctctgctg agcgaggctg tgctgagagg acaggccctg    240
ctcgtgaact cctcccagcc ttgggaaccc ctgcagctgc acgtggacaa ggctgtgtcc    300
ggcctgagat ccctgaccac cctgctgaga gcactgggag cccagaaaga ggccatctct    360
ccacctgacg ccgcctctgc tgctcctctg agaaccatca ccgccgacac cttcagaaag    420
ctgttccggg tgtactccaa cttcacgcgg ggcaagctga agctgtacac cggcgaggct    480
tgccggaccg gcgac                                                     495
```

```
<210> SEQ ID NO 22
<211> LENGTH: 165
<212> TYPE: PRT
<213> ORGANISM: Artificial Sequence
<220> FEATURE:
<223> OTHER INFORMATION: AA - MUTEIN 149

<400> SEQUENCE: 22

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Thr Arg Gly Lys Leu Lys Leu Tyr Thr Gly Glu Ala
145                 150                 155                 160

Cys Arg Thr Gly Asp
                165
```

```
<210> SEQ ID NO 23
<211> LENGTH: 495
<212> TYPE: DNA
<213> ORGANISM: Artificial Sequence
<220> FEATURE:
<223> OTHER INFORMATION: DNA - MUTEIN 151_153

<400> SEQUENCE: 23
gctcctccta gactgatctg cgactcccgg gtgctggaaa gatacctgct ggaagccaaa     60
gaggccgaga acatcaccac cggctgcgcc gagcactgct ccctgaacga gaatatcacc    120
gtgcccgaca ccaaagtgaa cttctacgcc tggaagcgga tggaagtggg ccagcaggct    180
gtggaagtgt ggcagggact ggctctgctg agcgaggctg tgctgagagg acaggccctg    240
ctcgtgaact cctcccagcc ttgggaaccc ctgcagctgc acgtggacaa ggctgtgtcc    300
ggcctgagat ccctgaccac cctgctgaga gcactgggag cccagaaaga ggccatctct    360
```

```
ccacctgacg ccgcctctgc tgctcctctg agaaccatca ccgccgacac cttcagaaag      420
ctgttccggg tgtactccaa cttcctgcgg aacaagacga agctgtacac cggcgaggct      480
tgccggaccg gcgac                                                      495
```

<210> SEQ ID NO 24
<211> LENGTH: 165
<212> TYPE: PRT
<213> ORGANISM: Artificial Sequence
<220> FEATURE:
<223> OTHER INFORMATION: AA - MUTEIN 151_153

<400> SEQUENCE: 24

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Asn Lys Thr Lys Leu Tyr Thr Gly Glu Ala
145                 150                 155                 160

Cys Arg Thr Gly Asp
                165
```

<210> SEQ ID NO 25
<211> LENGTH: 495
<212> TYPE: DNA
<213> ORGANISM: Homo sapiens
<220> FEATURE:
<223> OTHER INFORMATION: DNA - hEPO

<400> SEQUENCE: 25

```
gctcctccta gactgatctg cgactcccgg gtgctggaaa gatacctgct ggaagccaaa       60
gaggccgaga acatcaccac cggctgcgcc gagcactgct ccctgaacga gaatatcacc      120
gtgcccgaca ccaaagtgaa cttctacgcc tggaagcgga tggaagtggg ccagcaggct      180
gtggaagtgt ggcagggact ggctctgctg agcgaggctg tgctgagagg acaggccctg      240
ctcgtgaact cctcccagcc ttgggaaccc ctgcagctgc acgtggacaa ggctgtgtcc      300
ggcctgagat ccctgaccac cctgctgaga gcactgggag cccagaaaga ggccatctct      360
ccacctgacg ccgcctctgc tgctcctctg agaaccatca ccgccgacac cttcagaaag      420
ctgttccggg tgtactccaa cttcctgcgg ggcaagctga agctgtacac cggcgaggct      480
tgccggaccg gcgac                                                      495
```

-continued

```
<210> SEQ ID NO 26
<211> LENGTH: 165
<212> TYPE: PRT
<213> ORGANISM: Homo sapiens
<220> FEATURE:
<223> OTHER INFORMATION: AA - hEPO

<400> SEQUENCE: 26

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```